United States Patent [19]

Inzana et al.

[11] Patent Number: 6,086,894
[45] Date of Patent: Jul. 11, 2000

[54] RECOMBINANT VACCINE FOR DISEASES CAUSED BY ENCAPSULATED ORGANISMS

[75] Inventors: Thomas J. Inzana, Blacksburg, Va.; Christine Ward, Irving, Tex.

[73] Assignee: Virginia Tech Intellectual Properties, Inc., Blacksburg, Va.

[21] Appl. No.: 08/673,814

[22] Filed: Jun. 27, 1996

[51] Int. Cl.[7] .............................. A61K 39/102; C12N 1/36
[52] U.S. Cl. .................. 424/235.1; 424/93.2; 424/256.1; 424/825; 424/932; 435/243; 435/245; 435/252.3; 435/172.3; 56/23.1; 56/24.32; 56/24.33
[58] Field of Search ................................ 424/93.2, 256.1, 424/825, 235.1, 932; 435/243, 245, 252.3, 172.3; 536/23.1, 24.32, 24.33

[56] References Cited

U.S. PATENT DOCUMENTS 5,429,818  7/1995  Inzana .

FOREIGN PATENT DOCUMENTS 9310815  10/1993  WIPO .

OTHER PUBLICATIONS

Frosch et al. (1991) Mol. Microbiol. vol. 5(5), 1251–1263.
Ley et al (1995) Vaccine vol. 13(4), 401–107.
Kozel et al (1992) Infect. & Immunity vol. 60(8), 3122–3127.

*Primary Examiner*—Anthony C. Caputa
*Assistant Examiner*—Khalid Masood
*Attorney, Agent, or Firm*—Whitham, Curtis, & Whitham

[57] ABSTRACT

Vaccines for diseases caused by normally encapsulated organisms are produced by genetically modifying those organisms by deleting the genes encoding for capsule synthesis or a portion thereof sufficient to produce non-capsulated mutants of the organisms. As an example, a live, attenuated strain of *Actinobacillus pleuropneumoniae* genetically modified with a large deletion in a chromosomal regions of the DNA which encodes for capsule synthesis is a safe and effective vaccine against swine pleuropneumonia.

4 Claims, 10 Drawing Sheets

```
AAGCTTGAGCAGGCAGCCAAACTAGCAACCAGCCCCAAAGAAAGGAGTAATCTAAGTTTGATGAGTTTCATCTAATTTCTCTTCAATATATTAAGGAATAACAAC      105

TATATAGGTATGTCTTAAAATCCACATAAAGATTGATTTTAATAAGTTACCTAATCAAGAGAAATTAAATATAAGAAATTTACAAACAAATTAAAAATGTATTT      210

-35
TTTTTAAAAAAAAGTAAATCAAGAGGGGCGTTATACAGATAAACATTATAATTTAAAAGCCATATAAAATACGGAGTTTCCCCTAGATAGTTGATAAATTTCTCA    315

-10
TTTATATTTATGAAATTCCGATGAAAAATTTATCAACTATCTAGGGTAACTCCATAACGTATTCGTATTTCAGGAGTATTTTTAATGTCTAGCATAATGACTCGT    420
                                                                   CpsA →   M S S I M T R
```

```

CCTATAATTAATCATGTAATGTCTAGAGATATTCAAAGTGGCATATTTAGTTCTATTTTAGAATATTTTACTGATTTTGGTTCCAATGAATTTCAACATATTGTC   525
```

```
 P I I N H V M S R D I Q S G I F S S I L E Y F T D F G S N E F Q H I V
ACTGTATCTCCAATACCTGAAGCTAAAGTTTATCACTATCACCGTCCACACCTAGAAGAAAAATTATTACCTAATTCTGTTTGTACAGTACATCATGACCTCAAT  630
```

```
 S V S P I P E A K V Y H Y H R P H L E E K L L P N S V C T V H H D L N
GATCCAGATCCTTGGCATGCTAAGTATAGATTTATTCCTAGATATATGGAAGCTGGGGCTATAATTTGTTTAAATTACACTCAAAAAGAAATTTTAATATCTCAG  735
```

```
 D P D P W H A K Y R F I P R Y M E A G A I I C L N Y T Q K E I L I S Q
GGACTTCCGGAACATAAGTTATTTGTGATTCCTCACGGATATAATCAAAAAGTATTATTTCCTAAGAAAATTAAAGAAATATCAAGTACAGATAAAATTACCTTA   840
```

```
 G L P E H K L F V I P H G Y N Q K V L F P K K I K E I S S T D K I T L
GGAATTGCTTCACGGAGATATGGTAGAAGAGTAAAAGGAGATGCATATTTATTTGAATTAGCAAAAAGATTAAATCCAGACCATTTTAAATTTATTTTTGTTGGT   945
```

```
 G I A S R R Y G R R V K G D A Y L F E L A K R L N P D H F K F I F V G
AAAGATAGACAATATAGTGCCTTAGAAATGCAAGATCTAGGATTTGAAGCTCAAGTATATGAAAGATTGCCATATAGAATGTTTCAAAGTTTTTATAATAATATT   1050
```

```
 K D R Q Y S A L E M Q D L G F E A Q V Y E R L P Y R M F Q S F Y N N I
GATGTACTACTTATGTGTAGTAGTCATGAAGGTGGACCTGCAAATATCCCCGAAGCATTAGCTACTGGGACACCTATATTTTCATCTAACATAGGTATACCTAAG   1155
```

```
 D V L L M C S S H E G G P A N I P E A L A T G T P I F S S N I G I P K
GATGTTGTTATTATTATAAGAATGGGTTGATTCTAACCTTAGATCCAGATATAGATGCTGAACAGATTAATTTTATTTGCCTTGAAAAACCAAATATATTTGAA   1260
```

```
 D V V I N Y K N G L I L T L D P D I D A E Q I N F I C L E K P N I F E
AATATATTAGATTTTTCACTAAAAACAGTCTCCAAGTTTAGCAATTTCTTGGGAGAAATGTATTCAACAAAATATTTTAGTTTATAAAAAAAATAATTAAGGGTTAA  1365
```

```
 N I L D F S L K Q S P S L A I S W E K C I Q Q N I L V Y K K I I K G
TTATGTCCATTTCTATTCTAGTACCTGATTCTTTACACATTAACAAAAGAAACTTTAGTTCATTCTTCAGTTGGATTGAGAAAAATAAAATAAATATCCATTTTG   1470
CpsB →
 M S I S I L V P D S L H I N K R N F S S F F S W I E K N K I N I H F
AAAATAATAATAAAGATTGGATTTCATTATATGGTTTTTACGATTCAAAATTGGGTATTCTATATGAGAAAATAGATATTCTTACTAAGATTGAAGAAGAGGAAT  1575
```

```
                                                                                                      1680
TATTTGCTTTTTGTGTTTATGATCTAAATATTTTCAATATTTGTAGAGCTGAATTATTATCTTTAGTAGCCACAAGACCCGAATGGTATAATGAAGATTATCCTA

L F A F C V Y D L N I F N I C R A E L L S L V A T R P E W Y N E D Y P
ATAACTTAAGAGAAATATACAAAAAACTCTATACTAATAATCGAAGTGAATTATTGCAAAACATGGCTGCTGCTTGGTATTGGGTTGATTTCTGGAAAAAACGCC
                                                                                                      1785

N N L R E I Y K K L Y T N N R S E L L Q N M A A A W W V D F W K K R
TATCTGAGTTAAAACAATTCTCTCATTGTTGTGTATTTTCAGGAGGTTTAATTTATCAAAAATCTTTGATTGAGTTATTAAAATATACTCCAACTAAAGTTATGG
                                                                                                      1890

L S E L K Q F S H C C V F S G G L I Y Q K S L I E L L K Y T P T K V M
TTATGGAAAGCCTATTTACAGGAAACGAATATTATTGTGAGGAACGTTATTCATCAATTGCTAATAATAGCGATATTAAACATTTAGCTATTTTTAACTCTTATA
                                                                                                      1995

V M E S L F T G N E Y Y C E E R Y S S I A N N S D I K H L A I F N S Y
AAAAAACATTTAGTTCAAAAAGTGAATATGATAAGGAACGAATGAAAGCTATTAATAAGTTCCTATTAATGAAAAATAAGAATGTCCAACAACCTACTGATTCTG
                                                                                                      2100

K K T F S S K S E Y D K E R M K A I N K F L L M K N K N V Q Q P T D S
AAATATTAGTATTTAAACAACAAAAACCAATAATTACTATTATTGGACAAGTGATAAATGATTTTTCAGTCCTAGAATATAAAGGGAGAGGACTATCAACAATTA
                                                                                                      2205

E I L V F K Q Q K P I I T I I G Q V I N D F S V L E Y K G R G L S T I
AAATCTATAAAGAACTTATATCTAAACTATCAGAGAATGGATTTAATGTAGTATTAAAAACTCACCCTTGGGAAGAGAAAAAAAATAATATCCGTACATCTTTAA
                                                                                                      2310

K I Y K E L I S K L S E N G F N V V L K T H P W E E K K N N I R T S L
CTAAAAATATAATAGAAGAATTTCTAAAAAATCTAACTGAGAATCAACAAGAATGTATAAAAATAGTTGATCACTATTCAATAAAGAAATTATTTAAACAATCTG
                                                                                                      2415

T K N I I E E F L K N L T E N Q Q E C I K I V D H Y S I K K L F K Q S
ATTTTATTATTAGTTTAAATTCTCAAGGGCTCCTTGAAGCTGCATTTGATGGTATAAAACCTATACAGTTAGGTAATGCTTTTTATGGAAAAAAAGGATTCACGT
                                                                                                      2520

D F I I S L N S Q G L L E A A F D G I K P I Q L G N A F Y G K K G F T
ACGATTATGACTTTTTAGATATTGATCAATTGGTAAATGACTTAGTAGTAAATAAACTTACTCCAACACTATCTTTAGAAGAGTTTGATTTGTTCGAAGAGTTCA
                                                                                                      2625

Y D Y D F L D I D Q L V N D L V V N K L T P T L S L E E F D L F E E F
TTACTATATTATTACAAAAGCATGCTGTTTCTATTCACGCCTCTGGCGTAAGTGTTTTATCTAGAATATTTAATTTACCTACTATTATACCATTAGTAGAAAATG
                                                                                                      2730

I T I L L Q K H A V S I H A S G V S V L S R I F N L P T I I P L V E N
TCCCTAAGGAGAAGTCTAAAACAACATTACCTACTCAAAAAGATGTGGTAAAAAAGGAAAATACAACAATTGTTAATATGGTTGAGTTACCTAAAGTAGTTCCAC
                                                                                                      2835

V P K E K S K T T L P T Q K D V V K K E N T T I V N M V E L P K V V P
AAAGTGATAAGAATAGGAAATATCAAAAATTTAGAAACAATCCTCGACAATTCTTTGCAGATTCTAGGAATCCAGTTATTAGAAGTTTAATGTATTTTTTCCCTT
                                                                                                      2940

Q S D K N R K Y Q K F R N N P R Q F F A D S R N P V I R S L M Y F F P
ATAAATAATATAGGTCTAATTTATGTTAAAAAAAATATCAGCCTTTTGATTTAAGAAAAATAAATGAAGGCCACTCTAGTAATGCTAAGTTAGTTTTACATTCTGA
                                                                                                      3045

Y K .  CpsC→ M L K K Y Q P F D L R K I N E G H S S N A K L V L H S E
GGCCTGTAATATAGATGCTAAAATCTCTAAGTTTTTCTGTTCACAAGATGACATTAATTTAGAAAACTTTATTGCAACATTTACTGATAACTATAAAGCACCAGA
                                                                                                      3150

A C N I D A K I S K F F C S Q D D I N L E N F I A T F T D N Y K A P E
AGTATATACGGCGATTTTAAAGAATTGTTGTATTACACCTAGAGCACCTAAGCTACCAAGAT
                                                                 3212
   V Y T A I L K N C C I T P R A P K L P R
```

FIG.3B

```
CTAGACATTACATGATTAATTATAGGACGAGTCATTATGCTAGACATTAAAAATACTCCTGAAATACGAATACGTTATGGAGTTACCCTA
                                                                                              90
GATAGTTGATAAATTTTTCATCGGAATTTCATAAATATAAATGAGAAATTTATCAACTATCTAGGGGAAACTCCGTATTTTATATGGCTT
                                                                                              180
TTAAATTATAATGTTTATCTGTATAACGCCCCTCTTGATTTACTTTTTTTAAAAAAAAATACATTTTTTAATTTGTTTGTAAATTTCTTA
                                                                                              270
             -35                    -10
TATTTAATTTCTCTTGATTAGGTAACTTATTAAAATCAATCTTTATGTGGATTTTAAGACATACCTATATAGTTGTTATTCCTTAATATA
                                                                                              360
TTGAAGAGAAATTAGATGAAACTCATCAAACTTAGATTACTCCTTTCTTTGGGGCTGGTTGCTAGTTTGGCTGCCTGCTCAAGCTTACCC
                                                                                              450
         CpxD →  M  K  L  I  K  L  R  L  L  L  S  L  G  L  V  A  S  L  A  A ▼ C  S  S  L  P
ACTTCAGGCCCTAGCCATAGTGCGATTTTAGAGGCTAATTCCCAGAACTCAGATAAACCTTTACCGGAAGTTAATTTAGTGGAGTTAGAT
                                                                                              540
  T  S  G  P  S  H  S  A  I  L  E  A  N  S  Q  N  S  D  K  P  L  P  E  V  N  L  V  E  L  D
AATGGCTTAGTTCAGCAGTTGTATCAGACTCAGCAAAGTCAGCAATTTTCCGGCTTTTTAGGCACGGCTGGCGGTGCTGGATATGCCGGT
                                                                                              630
  N  G  L  V  Q  Q  L  Y  Q  T  Q  Q  S  Q  Q  F  S  G  F  L  G  T  A  G  G  A  G  Y  A  G
GCGGTCAATGTGGGGGATGTTCTTGAAATTTCAATTTGGGAAGCGCCACCGGCAGTGTTGTTTGGCGGTACTTTTAGTTCTGAAGGGCAA
                                                                                              720
  A  V  N  V  G  D  V  L  E  I  S  I  W  E  A  P  P  A  V  L  F  G  G  T  F  S  S  E  G  Q
GGTAGCGGGCATTTAACGCAATTACCGGCGCAAATGGTTAACCAAAACGGTACGGTTACTGTGCCGTTTGTGGGTAATATTCGTGTTGCA
                                                                                              810
  G  S  G  H  L  T  Q  L  P  A  Q  M  V  N  Q  N  G  T  V  T  V  P  F  V  G  N  I  R  V  A
GGTAAAACACCGGAAGCGATTCAGTCTCAAATTGTTGGGGCATTGCAACGTAAAGCGAATCAGCCACAAGTATTAGTAAAAATTGCGAAT
                                                                                              900
  G  K  T  P  E  A  I  Q  S  Q  I  V  G  A  L  Q  R  K  A  N  Q  P  Q  V  L  V  K  I  A  N
AATAACTCTGCGGATGTTACGGTTATTCGTCAGGGTAACAGTATTCGTATGCCGCTGAGTGCGAATAACGAACGTGTGTTAGATGCTGTT
                                                                                              990
  N  N  S  A  D  V  T  V  I  R  Q  G  N  S  I  R  M  P  L  S  A  N  N  E  R  V  L  D  A  V
GCAGCAGTAGGCGGTACAACTGAAAATATTGAAGACGTTACCGTAAAATTAACTCGTGGCTCGCAAGTCAAAACATTAGCGTTTGAAACT
                                                                                              1080
  A  A  V  G  T  T  E  N  I  E  D  V  T  V  K  L  T  R  G  S  Q  V  K  T  L  A  F  E  T
CTAATTTCCGATCCGGCGCAAAATATTATGTACGTGCCGGCGATGTCGTTTCGTTGCTAAACACGCCTTATAGCTTTACCGGTTTAGGT
                                                                                              1170
  L  I  S  D  P  A  Q  N  I  M  L  R  A  G  D  V  V  S  L  L  N  T  P  Y  S  F  T  G  L  G
GCGGTGGGTAACAACCAGCAAATGAAATTCTCAAGTAAAGGAATTACGCTTGCCGAAGCTATCGGTAAGATGGGTGGCCTAATTGATACT
                                                                                              1260
  A  V  G  N  N  Q  Q  M  K  F  S  S  K  G  I  T  L  A  E  A  I  G  K  M  G  G  L  I  D  T
CGTTCGGATCCGAGAGGGGTATTCGTCTTCCGTCATGTGCCTTTTTCTCAATTAAGTTTAGATCAGCAAACACAATGGGAGCGAAAGGC
                                                                                              1350
  R  S  D  P  R  G  V  F  V  F  R  H  V  P  F  S  Q  L  S  L  D  Q  Q  T  Q  W  G  A  K  G
TATGGTATGGGTATGGATGTACCGACGGTTTATCGTGTGAATTTACTTGAGCCGCAATCACTGTTTTTATTACAACGCTTCCCGATGCAA
                                                                                              1440
  Y  G  M  G  M  D  V  P  T  V  Y  R  V  N  L  L  E  P  Q  S  L  F  L  L  Q  R  F  P  M  Q
GATAAAGATATTGTCTATGTATCAAATGCACCGTTGTCCGAATTCCAAAAAATTCTTGAGAATGATTTTCTCGATTACTTCGCCGGTTACA
                                                                                              1530
  D  K  D  I  V  Y  V  S  N  A  P  L  S  E  F  Q  K  F  L  R  M  I  F  S  I  T  S  P  V  T
```

FIG.10A

```
AGTACGACTAATGCTATTCGTGCCTATTAATATATTGAATTTATAAGGATAAAATATGGAAACAACTATTACGGCAAGTCCGACAGAAAA
                                                                                              1620
  S  T  T  N  A  I  R  A  Y  .           CpxC →  M  E  T  T  I  T  A  S  P  T  E  K
ACTACAAAAACCGGTTAAACAGAAAAAAAGTTGGTTAAAAAAGCTTAATCCGTTATTTTGGGTAACTGTAGCGATTCCTACGGTATTATC
                                                                                              1710
  L  Q  K  P  V  K  Q  K  K  S  W  L  K  K  L  N  P  L  F  W  V  T  V  A  I  P  T  V  L  S
AGCCTTTTATTTCGGTTCTGTTGCTTCCGATATTTATATTTCGGAATCAAGCTTCGTTGTAAGATCTCCTCAAAATCAGACCGCTTTAAC
                                                                                              1800
  A  F  Y  F  G  S  V  A  S  D  I  Y  I  S  E  S  S  F  V  V  R  S  P  Q  N  Q  T  A  L  T
CGGTGTCGGTGCCTTATTACAAGGTTCCGGATTTTCTCGAGCTCAAGATGATACTTATACCGTACAAGAATATATGCATTCTCGTACGGC
                                                                                              1890
  G  V  G  A  L  L  Q  G  S  G  F  S  R  A  Q  D  D  T  Y  T  V  Q  E  Y  M  H  S  R  T  A
ACTAGAACAGTTAATGAAAGACTTGCCAATACGTGAATACTATGAGAATCAAGGCGATATTATCGCTCGCTTTAATGGATTTGGTTTAAA
                                                                                              1980
  L  E  Q  L  M  K  D  L  P  I  R  E  Y  Y  E  N  Q  G  D  I  I  A  R  F  N  G  F  G  L  N
TAATAGTAAAGAAGCGTTTTATAAATATTTCCGAGATCGCTTAAGTGTGGACTTTGACTCTGTTTCCGGTATCGCCAGCTTACGTATTCG
                                                                                              2070
  N  S  K  E  A  F  Y  K  Y  F  R  D  R  L  S  V  D  F  D  S  V  S  G  I  A  S  L  R  I  R
AGCATTTAACGCGGAAGAGGGGCAACAAATTAATCAAAAATTACTTGCCGAAGGTGAAACGCTTATTAACCGTTTAAACGAACGTGCAAG
                                                                                              2160
  A  F  N  A  E  E  G  Q  Q  I  N  Q  K  L  L  A  E  G  E  T  L  I  N  R  L  N  E  R  A  R
AAAAGATACCATTTCATTTGCGGAACAAGCGGTTACAGAAGCGGAAAATAATGTAAACGAAACGGAAATGCTTTAAGTAAATACCGTAT
                                                                                              2250
  K  D  T  I  S  F  A  E  Q  A  V  T  E  A  E  N  N  V  N  E  T  A  N  A  L  S  K  Y  R  I
CAAAAATAAAATCTTTGATTTACCGGCACAATCCGGCGTACAACTTTCATTAATTTCCAGCCTAAAAAGCGAATTGATTCGTGTAGAAAC
                                                                                              2340
  K  N  K  I  F  D  L  P  A  Q  S  G  V  Q  L  S  L  I  S  S  L  K  S  E  L  I  R  V  E  T
ACAATTGGCTCAATTGCAATCTATTACACCGGACAACCCACAAGTTGATGCATTGCTTATGCGCCAAAAAAGTTTACGTAAGGAAATCGA
                                                                                              2430
  Q  L  A  Q  L  Q  S  I  T  P  D  N  P  Q  V  D  A  L  L  M  R  Q  K  S  L  R  K  E  I  D
TGAGCAATCAAAACAGCTTTCCAGTAACAGTAATAGCTCTATTGCTATTCAAACTGCCGATTACCACCGCTTAGTACTTGCAAACGAGCT
                                                                                              2520
  E  Q  S  K  Q  L  S  S  N  S  N  S  S  I  A  I  Q  T  A  D  Y  Q  R  L  V  L  A  N  E  L
GGCACAGCAACAATTGACCGCAGCATTAACCTCATTACAAAATACGAAAAATGAAGCGGATCGCCAGCAACTTTATTTAGAAGTAATCAG
                                                                                              2610
  A  Q  Q  Q  L  T  A  A  L  T  S  L  Q  N  T  K  N  E  A  D  R  Q  Q  L  Y  L  E  V  I
TCAGCCAAGCAAACCGGACTGGGCGGAAGAGCCTTATCGCTTATATAATATTTTAGCGACATTCTTTATCGGTCTGATGCTTTATGGTGT
                                                                                              2700
  Q  P  S  K  P  D  W  A  E  E  P  Y  R  L  Y  N  I  L  A  T  F  F  I  G  L  M  L  Y  G  V
ATTAAGTTTATTAATTGCAAGCGTAAGAGAGCACAAAAAACTAATGCAATACGGTGATCAAACAACTTTCCGCCAATCTCTCGCCATTCAA
                                                                                              2790
  L  S  L  L  I  A  S  V  R  E  H  K  N  .
                                       CpxB →  M  Q  Y  G  D  Q  T  T  F  R  Q  S  L  A  I  Q
GGGAGAGTAATCGGTGCATTACTCATGCGGGAAATTATTACGCGTTACGGACGAAAAAATTTGGGTTTTTTATGGCTGTTTGTTGAGCCG
                                                                                              2880
  G  R  V  I  G  A  L  L  M  R  E  I  I  T  R  Y  G  R  K  N  L  G  F  L  W  L  F  V  E  P
CTATTACTCACTTTATTTATCGTTTTGATGTGGAAATTTATCCGAGCGGATCGCGTTTCCGATTTAAATATTATTGCTTTTGTGATTACC
                                                                                              2970
  L  L  L  T  L  F  I  V  L  M  W  K  F  I  R  A  D  R  V  S  D  L  N  I  A  F  V  I  T
GGTTATCCAATGGCCATGATGTGGCGTAATGCGTCAAACCGCACTATCGGTGCAATTTCCGGTAACTTGAGTCTTCTTTATCATCGTAAT
                                                                                              3060
  G  Y  P  M  A  M  M  W  R  N  A  S  N  R  T  I  G  A  I  S  G  N  L  S  L  L  Y  H  R  N
GTTCGCGTATTAGATACCTTACTGGCTCGTGTCATACTTGAAGTAGCAGGTGCAACGATTGCCCAAATCATTATTATGGCATTAGTCATT
                                                                                              3150
  V  R  V  L  D  T  L  L  A  R  V  I  L  E  V  A  G  A  T  I  A  Q  I  I  I  M  A  L  V  I
```

FIG.10B

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 3212 base pairs
      (B) TYPE: nucleic acid
      (C) STRANDEDNESS: single
      (D) TOPOLOGY: linear (ix) FEATURE:
      (A) NAME/KEY: CDS
      (B) LOCATION: 400..1362

(ix) FEATURE:
      (A) NAME/KEY: CDS
      (B) LOCATION: 1368..2945

(ix) FEATURE:
      (A) NAME/KEY: CDS
      (B) LOCATION: 2963..3211

(xi) SEQUENCE DESCRIPTION: SEQ ID NO:1:

```
AAGCTTGAGC AGGCAGCCAA ACTAGCAACC AGCCCCAAAG AAAGGAGTAA TCTAAGTTTG      60

ATGAGTTTCA TCTAATTTCT CTTCAATATA TTAAGGAATA ACAACTATAT AGGTATGTCT     120

TAAAATCCAC ATAAAGATTG ATTTTAATAA GTTACCTAAT CAAGAGAAAT TAAATATAAG     180

AAATTTACAA ACAAATTAAA AAATGTATTT TTTTTAAAAA AAAGTAAATC AAGAGGGGCG     240
```

-continued

```
TTATACAGAT AAACATTATA ATTTAAAAGC CATATAAAAT ACGGAGTTTC CCCTAGATAG      300

TTGATAAATT TCTCATTTAT ATTTATGAAA TTCCGATGAA AAATTTATCA ACTATCTAGG      360

GTAACTCCAT AACGTATTCG TATTTCAGGA GTATTTTTA ATG TCT AGC ATA ATG         414
                                             Met Ser Ser Ile Met
                                              1               5

ACT CGT CCT ATA ATT AAT CAT GTA ATG TCT AGA GAT ATT CAA AGT GGC        462
Thr Arg Pro Ile Ile Asn His Val Met Ser Arg Asp Ile Gln Ser Gly
            10                  15                  20

ATA TTT AGT TCT ATT TTA GAA TAT TTT ACT GAT TTT GGT TCC AAT GAA        510
Ile Phe Ser Ser Ile Leu Glu Tyr Phe Thr Asp Phe Gly Ser Asn Glu
                25                  30                  35

TTT CAA CAT ATT GTC AGT GTA TCT CCA ATA CCT GAA GCT AAA GTT TAT        558
Phe Gln His Ile Val Ser Val Ser Pro Ile Pro Glu Ala Lys Val Tyr
        40                  45                  50

CAC TAT CAC CGT CCA CAC CTA GAA GAA AAA TTA TTA CCT AAT TCT GTT        606
His Tyr His Arg Pro His Leu Glu Glu Lys Leu Leu Pro Asn Ser Val
    55                  60                  65

TGT ACA GTA CAT CAT GAC CTC AAT GAT CCA GAT CCT TGG CAT GCT AAG        654
Cys Thr Val His His Asp Leu Asn Asp Pro Asp Pro Trp His Ala Lys
70                  75                  80                  85

TAT AGA TTT ATT CCT AGA TAT ATG GAA GCT GGG GCT ATA ATT TGT TTA        702
Tyr Arg Phe Ile Pro Arg Tyr Met Glu Ala Gly Ala Ile Ile Cys Leu
                90                  95                 100

AAT TAC ACT CAA AAA GAA ATT TTA ATA TCT CAG GGA CTT CCG GAA CAT        750
Asn Tyr Thr Gln Lys Glu Ile Leu Ile Ser Gln Gly Leu Pro Glu His
            105                 110                 115

AAG TTA TTT GTG ATT CCT CAC GGA TAT AAT CAA AAA GTA TTA TTT CCT        798
Lys Leu Phe Val Ile Pro His Gly Tyr Asn Gln Lys Val Leu Phe Pro
        120                 125                 130

AAG AAA ATT AAA GAA ATA TCA AGT ACA GAT AAA ATT ACC TTA GGA ATT        846
Lys Lys Ile Lys Glu Ile Ser Ser Thr Asp Lys Ile Thr Leu Gly Ile
    135                 140                 145

GCT TCA CGG AGA TAT GGT AGA AGA GTA AAA GGA GAT GCA TAT TTA TTT        894
Ala Ser Arg Arg Tyr Gly Arg Arg Val Lys Gly Asp Ala Tyr Leu Phe
150                 155                 160                 165

GAA TTA GCA AAA AGA TTA AAT CCA GAC CAT TTT AAA TTT ATT TTT GTT        942
Glu Leu Ala Lys Arg Leu Asn Pro Asp His Phe Lys Phe Ile Phe Val
                170                 175                 180

GGT AAA GAT AGA CAA TAT AGT GCC TTA GAA ATG CAA GAT CTA GGA TTT        990
Gly Lys Asp Arg Gln Tyr Ser Ala Leu Glu Met Gln Asp Leu Gly Phe
            185                 190                 195

GAA GCT CAA GTA TAT GAA AGA TTG CCA TAT AGA ATG TTT CAA AGT TTT       1038
Glu Ala Gln Val Tyr Glu Arg Leu Pro Tyr Arg Met Phe Gln Ser Phe
        200                 205                 210

TAT AAT AAT ATT GAT GTA CTA CTT ATG TGT AGT AGT CAT GAA GGT GGA       1086
Tyr Asn Asn Ile Asp Val Leu Leu Met Cys Ser Ser His Glu Gly Gly
    215                 220                 225

CCT GCA AAT ATC CCC GAA GCA TTA GCT ACT GGG ACA CCT ATA TTT TCA       1134
Pro Ala Asn Ile Pro Glu Ala Leu Ala Thr Gly Thr Pro Ile Phe Ser
230                 235                 240                 245

TCT AAC ATA GGT ATA CCT AAG GAT GTT GTT ATT AAT TAT AAG AAT GGG       1182
Ser Asn Ile Gly Ile Pro Lys Asp Val Val Ile Asn Tyr Lys Asn Gly
                250                 255                 260

TTG ATT CTA ACC TTA GAT CCA GAT ATA GAT GCT GAA CAG ATT AAT TTT       1230
Leu Ile Leu Thr Leu Asp Pro Asp Ile Asp Ala Glu Gln Ile Asn Phe
            265                 270                 275

ATT TGC CTT GAA AAA CCA AAT ATA TTT GAA AAT ATA TTA GAT TTT TCA       1278
Ile Cys Leu Glu Lys Pro Asn Ile Phe Glu Asn Ile Leu Asp Phe Ser
        280                 285                 290
```

```
CTA AAA CAG TCT CCA AGT TTA GCA ATT TCT TGG GAG AAA TGT ATT CAA      1326
Leu Lys Gln Ser Pro Ser Leu Ala Ile Ser Trp Glu Lys Cys Ile Gln
    295             300             305

CAA AAT ATT TTA GTT TAT AAA AAA ATA ATT AAG GGT TAATT ATG TCC        1373
Gln Asn Ile Leu Val Tyr Lys Lys Ile Ile Lys Gly      Met Ser
310             315             320                      1

ATT TCT ATT CTA GTA CCT GAT TCT TTA CAC ATT AAC AAA AGA AAC TTT      1421
Ile Ser Ile Leu Val Pro Asp Ser Leu His Ile Asn Lys Arg Asn Phe
          5             10              15

AGT TCA TTC TTC AGT TGG ATT GAG AAA AAT AAA ATA AAT ATC CAT TTT      1469
Ser Ser Phe Phe Ser Trp Ile Glu Lys Asn Lys Ile Asn Ile His Phe
     20              25              30

GAA AAT AAT AAT AAA GAT TGG ATT TCA TTA TAT GGT TTT TAC GAT TCA      1517
Glu Asn Asn Asn Lys Asp Trp Ile Ser Leu Tyr Gly Phe Tyr Asp Ser
 35              40              45                  50

AAA TTG GGT ATT CTA TAT GAG AAA ATA GAT ATT CTT ACT AAG ATT GAA      1565
Lys Leu Gly Ile Leu Tyr Glu Lys Ile Asp Ile Leu Thr Lys Ile Glu
                 55              60              65

GAA GAG GAA TTA TTT GCT TTT TGT GTT TAT GAT CTA AAT ATT TTC AAT      1613
Glu Glu Glu Leu Phe Ala Phe Cys Val Tyr Asp Leu Asn Ile Phe Asn
             70              75              80

ATT TGT AGA GCT GAA TTA TTA TCT TTA GTA GCC ACA AGA CCC GAA TGG      1661
Ile Cys Arg Ala Glu Leu Leu Ser Leu Val Ala Thr Arg Pro Glu Trp
         85              90              95

TAT AAT GAA GAT TAT CCT AAT AAC TTA AGA GAA ATA TAC AAA AAA CTC      1709
Tyr Asn Glu Asp Tyr Pro Asn Asn Leu Arg Glu Ile Tyr Lys Lys Leu
     100             105             110

TAT ACT AAT AAT CGA AGT GAA TTA TTG CAA AAC ATG GCT GCT GCT TGG      1757
Tyr Thr Asn Asn Arg Ser Glu Leu Leu Gln Asn Met Ala Ala Ala Trp
115             120             125             130

TAT TGG GTT GAT TTC TGG AAA AAA CGC CTA TCT GAG TTA AAA CAA TTC      1805
Tyr Trp Val Asp Phe Trp Lys Lys Arg Leu Ser Glu Leu Lys Gln Phe
             135             140             145

TCT CAT TGT TGT GTA TTT TCA GGA GGT TTA ATT TAT CAA AAA TCT TTG      1853
Ser His Cys Cys Val Phe Ser Gly Gly Leu Ile Tyr Gln Lys Ser Leu
         150             155             160

ATT GAG TTA TTA AAA TAT ACT CCA ACT AAA GTT ATG GTT ATG GAA AGC      1901
Ile Glu Leu Leu Lys Tyr Thr Pro Thr Lys Val Met Val Met Glu Ser
     165             170             175

CTA TTT ACA GGA AAC GAA TAT TAT TGT GAG GAA CGT TAT TCA TCA ATT      1949
Leu Phe Thr Gly Asn Glu Tyr Tyr Cys Glu Glu Arg Tyr Ser Ser Ile
180             185             190

GCT AAT AAT AGC GAT ATT AAA CAT TTA GCT ATT TTT AAC TCT TAT AAA      1997
Ala Asn Asn Ser Asp Ile Lys His Leu Ala Ile Phe Asn Ser Tyr Lys
195             200             205             210

AAA ACA TTT AGT TCA AAA AGT GAA TAT GAT AAG GAA CGA ATG AAA GCT      2045
Lys Thr Phe Ser Ser Lys Ser Glu Tyr Asp Lys Glu Arg Met Lys Ala
             215             220             225

ATT AAT AAG TTC CTA TTA ATG AAA AAT AAG AAT GTC CAA CAA CCT ACT      2093
Ile Asn Lys Phe Leu Leu Met Lys Asn Lys Asn Val Gln Gln Pro Thr
         230             235             240

GAT TCT GAA ATA TTA GTA TTT AAA CAA CAA AAA CCA ATA ATT ACT ATT      2141
Asp Ser Glu Ile Leu Val Phe Lys Gln Gln Lys Pro Ile Ile Thr Ile
     245             250             255

ATT GGA CAA GTG ATA AAT GAT TTT TCA GTC CTA GAA TAT AAA GGG AGA      2189
Ile Gly Gln Val Ile Asn Asp Phe Ser Val Leu Glu Tyr Lys Gly Arg
260             265             270

GGA CTA TCA ACA ATT AAA ATC TAT AAA GAA CTT ATA TCT AAA CTA TCA      2237
Gly Leu Ser Thr Ile Lys Ile Tyr Lys Glu Leu Ile Ser Lys Leu Ser
```

```
                275                 280                 285                 290
GAG AAT GGA TTT AAT GTA GTA TTA AAA ACT CAC CCT TGG GAA GAG AAA              2285
Glu Asn Gly Phe Asn Val Val Leu Lys Thr His Pro Trp Glu Glu Lys
                        295                 300                 305

AAA AAT AAT ATC CGT ACA TCT TTA ACT AAA AAT ATA ATA GAA GAA TTT              2333
Lys Asn Asn Ile Arg Thr Ser Leu Thr Lys Asn Ile Ile Glu Glu Phe
                        310                 315                 320

CTA AAA AAT CTA ACT GAG AAT CAA CAA GAA TGT ATA AAA ATA GTT GAT              2381
Leu Lys Asn Leu Thr Glu Asn Gln Gln Glu Cys Ile Lys Ile Val Asp
                        325                 330                 335

CAC TAT TCA ATA AAG AAA TTA TTT AAA CAA TCT GAT TTT ATT ATT AGT              2429
His Tyr Ser Ile Lys Lys Leu Phe Lys Gln Ser Asp Phe Ile Ile Ser
                        340                 345                 350

TTA AAT TCT CAA GGG CTC CTT GAA GCT GCA TTT GAT GGT ATA AAA CCT              2477
Leu Asn Ser Gln Gly Leu Leu Glu Ala Ala Phe Asp Gly Ile Lys Pro
355                     360                 365                 370

ATA CAG TTA GGT AAT GCT TTT TAT GGA AAA AAA GGA TTC ACG TAC GAT              2525
Ile Gln Leu Gly Asn Ala Phe Tyr Gly Lys Lys Gly Phe Thr Tyr Asp
                        375                 380                 385

TAT GAC TTT TTA GAT ATT GAT CAA TTG GTA AAT GAC TTA GTA GTA AAT              2573
Tyr Asp Phe Leu Asp Ile Asp Gln Leu Val Asn Asp Leu Val Val Asn
                        390                 395                 400

AAA CTT ACT CCA ACA CTA TCT TTA GAA GAG TTT GAT TTG TTC GAA GAG              2621
Lys Leu Thr Pro Thr Leu Ser Leu Glu Glu Phe Asp Leu Phe Glu Glu
                        405                 410                 415

TTC ATT ACT ATA TTA TTA CAA AAG CAT GCT GTT TCT ATT CAC GCC TCT              2669
Phe Ile Thr Ile Leu Leu Gln Lys His Ala Val Ser Ile His Ala Ser
                        420                 425                 430

GGC GTA AGT GTT TTA TCT AGA ATA TTT AAT TTA CCT ACT ATT ATA CCA              2717
Gly Val Ser Val Leu Ser Arg Ile Phe Asn Leu Pro Thr Ile Ile Pro
435                     440                 445                 450

TTA GTA GAA AAT GTC CCT AAG GAG AAG TCT AAA ACA ACA TTA CCT ACT              2765
Leu Val Glu Asn Val Pro Lys Glu Lys Ser Lys Thr Thr Leu Pro Thr
                        455                 460                 465

CAA AAA GAT GTG GTA AAA AAG GAA AAT ACA ACA ATT GTT AAT ATG GTT              2813
Gln Lys Asp Val Val Lys Lys Glu Asn Thr Thr Ile Val Asn Met Val
                        470                 475                 480

GAG TTA CCT AAA GTA GTT CCA CAA AGT GAT AAG AAT AGG AAA TAT CAA              2861
Glu Leu Pro Lys Val Val Pro Gln Ser Asp Lys Asn Arg Lys Tyr Gln
                        485                 490                 495

AAA TTT AGA AAC AAT CCT CGA CAA TTC TTT GCA GAT TCT AGG AAT CCA              2909
Lys Phe Arg Asn Asn Pro Arg Gln Phe Phe Ala Asp Ser Arg Asn Pro
                500                 505                 510

GTT ATT AGA AGT TTA ATG TAT TTT TTC CCT TAT AAA TAATATAGGT                   2955
Val Ile Arg Ser Leu Met Tyr Phe Phe Pro Tyr Lys
515                     520                 525

CTAATTT ATG TTA AAA AAA TAT CAG CCT TTT GAT TTA AGA AAA ATA AAT              3004
        Met Leu Lys Lys Tyr Gln Pro Phe Asp Leu Arg Lys Ile Asn
        1               5                   10

GAA GGC CAC TCT AGT AAT GCT AAG TTA GTT TTA CAT TCT GAG GCC TGT              3052
Glu Gly His Ser Ser Asn Ala Lys Leu Val Leu His Ser Glu Ala Cys
15                      20                  25                  30

AAT ATA GAT GCT AAA ATC TCT AAG TTT TTC TGT TCA CAA GAT GAC ATT              3100
Asn Ile Asp Ala Lys Ile Ser Lys Phe Phe Cys Ser Gln Asp Asp Ile
                        35                  40                  45

AAT TTA GAA AAC TTT ATT GCA ACA TTT ACT GAT AAC TAT AAA GCA CCA              3148
Asn Leu Glu Asn Phe Ile Ala Thr Phe Thr Asp Asn Tyr Lys Ala Pro
                50                  55                  60
```

```
GAA GTA TAT ACG GCG ATT TTA AAG AAT TGT TGT ATT ACA CCT AGA GCA              3196
Glu Val Tyr Thr Ala Ile Leu Lys Asn Cys Cys Ile Thr Pro Arg Ala
        65                  70                  75

CCT AAG CTA CCA AGA T                                                        3212
Pro Lys Leu Pro Arg
    80

(2) INFORMATION FOR SEQ ID NO:2:

(i) SEQUENCE CHARACTERISTICS:
        (A) LENGTH: 321 amino acids
        (B) TYPE: amino acid
        (D) TOPOLOGY: linear (ii) MOLECULE TYPE: protein (xi) SEQUENCE DESCRIPTION: SEQ ID NO:2:

Met Ser Ser Ile Met Thr Arg Pro Ile Ile Asn His Val Met Ser Arg
 1               5                  10                  15

Asp Ile Gln Ser Gly Ile Phe Ser Ser Ile Leu Glu Tyr Phe Thr Asp
                20                  25                  30

Phe Gly Ser Asn Glu Phe Gln His Ile Val Ser Val Ser Pro Ile Pro
            35                  40                  45

Glu Ala Lys Val Tyr His Tyr His Arg Pro His Leu Glu Glu Lys Leu
        50                  55                  60

Leu Pro Asn Ser Val Cys Thr Val His His Asp Leu Asn Asp Pro Asp
65                  70                  75                  80

Pro Trp His Ala Lys Tyr Arg Phe Ile Pro Arg Tyr Met Glu Ala Gly
                85                  90                  95

Ala Ile Ile Cys Leu Asn Tyr Thr Gln Lys Glu Ile Leu Ile Ser Gln
            100                 105                 110

Gly Leu Pro Glu His Lys Leu Phe Val Ile Pro His Gly Tyr Asn Gln
        115                 120                 125

Lys Val Leu Phe Pro Lys Lys Ile Lys Glu Ile Ser Ser Thr Asp Lys
    130                 135                 140

Ile Thr Leu Gly Ile Ala Ser Arg Arg Tyr Gly Arg Arg Val Lys Gly
145                 150                 155                 160

Asp Ala Tyr Leu Phe Glu Leu Ala Lys Arg Leu Asn Pro Asp His Phe
                165                 170                 175

Lys Phe Ile Phe Val Gly Lys Asp Arg Gln Tyr Ser Ala Leu Glu Met
            180                 185                 190

Gln Asp Leu Gly Phe Glu Ala Gln Val Tyr Glu Arg Leu Pro Tyr Arg
        195                 200                 205

Met Phe Gln Ser Phe Tyr Asn Asn Ile Asp Val Leu Leu Met Cys Ser
    210                 215                 220

Ser His Glu Gly Gly Pro Ala Asn Ile Pro Glu Ala Leu Ala Thr Gly
225                 230                 235                 240

Thr Pro Ile Phe Ser Ser Asn Ile Gly Ile Pro Lys Asp Val Val Ile
                245                 250                 255

Asn Tyr Lys Asn Gly Leu Ile Leu Thr Leu Asp Pro Asp Ile Asp Ala
            260                 265                 270

Glu Gln Ile Asn Phe Ile Cys Leu Glu Lys Pro Asn Ile Phe Glu Asn
        275                 280                 285

Ile Leu Asp Phe Ser Leu Lys Gln Ser Pro Ser Leu Ala Ile Ser Trp
    290                 295                 300

Glu Lys Cys Ile Gln Gln Asn Ile Leu Val Tyr Lys Lys Ile Ile Lys
305                 310                 315                 320
```

Gly (2) INFORMATION FOR SEQ ID NO:3:

(i) SEQUENCE CHARACTERISTICS:
        (A) LENGTH: 526 amino acids
        (B) TYPE: amino acid
        (D) TOPOLOGY: linear (ii) MOLECULE TYPE: protein (xi) SEQUENCE DESCRIPTION: SEQ ID NO:3:

```
Met Ser Ile Ser Ile Leu Val Pro Asp Ser Leu His Ile Asn Lys Arg
 1               5                  10                  15

Asn Phe Ser Ser Phe Phe Ser Trp Ile Glu Lys Asn Lys Ile Asn Ile
                20                  25                  30

His Phe Glu Asn Asn Asn Lys Asp Trp Ile Ser Leu Tyr Gly Phe Tyr
            35                  40                  45

Asp Ser Lys Leu Gly Ile Leu Tyr Glu Lys Ile Asp Ile Leu Thr Lys
        50                  55                  60

Ile Glu Glu Glu Glu Leu Phe Ala Phe Cys Val Tyr Asp Leu Asn Ile
 65                 70                  75                  80

Phe Asn Ile Cys Arg Ala Glu Leu Leu Ser Leu Val Ala Thr Arg Pro
                85                  90                  95

Glu Trp Tyr Asn Glu Asp Tyr Pro Asn Asn Leu Arg Glu Ile Tyr Lys
                100                 105                 110

Lys Leu Tyr Thr Asn Asn Arg Ser Glu Leu Leu Gln Asn Met Ala Ala
            115                 120                 125

Ala Trp Tyr Trp Val Asp Phe Trp Lys Lys Arg Leu Ser Glu Leu Lys
        130                 135                 140

Gln Phe Ser His Cys Cys Val Phe Ser Gly Gly Leu Ile Tyr Gln Lys
145                 150                 155                 160

Ser Leu Ile Glu Leu Leu Lys Tyr Thr Pro Thr Lys Val Met Val Met
                165                 170                 175

Glu Ser Leu Phe Thr Gly Asn Glu Tyr Tyr Cys Glu Glu Arg Tyr Ser
                180                 185                 190

Ser Ile Ala Asn Asn Ser Asp Ile Lys His Leu Ala Ile Phe Asn Ser
            195                 200                 205

Tyr Lys Lys Thr Phe Ser Ser Lys Ser Glu Tyr Asp Lys Glu Arg Met
        210                 215                 220

Lys Ala Ile Asn Lys Phe Leu Leu Met Lys Asn Lys Asn Val Gln Gln
225                 230                 235                 240

Pro Thr Asp Ser Glu Ile Leu Val Phe Lys Gln Lys Pro Ile Ile
                245                 250                 255

Thr Ile Ile Gly Gln Val Ile Asn Asp Phe Ser Val Leu Glu Tyr Lys
                260                 265                 270

Gly Arg Gly Leu Ser Thr Ile Lys Ile Tyr Lys Glu Leu Ile Ser Lys
            275                 280                 285

Leu Ser Glu Asn Gly Phe Asn Val Val Leu Lys Thr His Pro Trp Glu
        290                 295                 300

Glu Lys Lys Asn Asn Ile Arg Thr Ser Leu Thr Lys Asn Ile Ile Glu
305                 310                 315                 320

Glu Phe Leu Lys Asn Leu Thr Glu Asn Gln Gln Glu Cys Ile Lys Ile
                325                 330                 335

Val Asp His Tyr Ser Ile Lys Lys Leu Phe Lys Gln Ser Asp Phe Ile
```

```
                    340                 345                 350
Ile Ser Leu Asn Ser Gln Gly Leu Leu Glu Ala Ala Phe Asp Gly Ile
                355                 360                 365
Lys Pro Ile Gln Leu Gly Asn Ala Phe Tyr Gly Lys Lys Gly Phe Thr
370                 375                 380
Tyr Asp Tyr Asp Phe Leu Asp Ile Asp Gln Leu Val Asn Asp Leu Val
385                 390                 395                 400
Val Asn Lys Leu Thr Pro Thr Leu Ser Leu Glu Glu Phe Asp Leu Phe
                405                 410                 415
Glu Glu Phe Ile Thr Ile Leu Leu Gln Lys His Ala Val Ser Ile His
                420                 425                 430
Ala Ser Gly Val Ser Val Leu Ser Arg Ile Phe Asn Leu Pro Thr Ile
                435                 440                 445
Ile Pro Leu Val Glu Asn Val Pro Lys Glu Lys Ser Lys Thr Thr Leu
450                 455                 460
Pro Thr Gln Lys Asp Val Val Lys Lys Glu Asn Thr Thr Ile Val Asn
465                 470                 475                 480
Met Val Glu Leu Pro Lys Val Val Pro Gln Ser Asp Lys Asn Arg Lys
                485                 490                 495
Tyr Gln Lys Phe Arg Asn Asn Pro Arg Gln Phe Phe Ala Asp Ser Arg
                500                 505                 510
Asn Pro Val Ile Arg Ser Leu Met Tyr Phe Phe Pro Tyr Lys
                515                 520                 525

(2) INFORMATION FOR SEQ ID NO:4:

(i) SEQUENCE CHARACTERISTICS:
         (A) LENGTH: 83 amino acids
         (B) TYPE: amino acid
         (D) TOPOLOGY: linear (ii) MOLECULE TYPE: protein (xi) SEQUENCE DESCRIPTION: SEQ ID NO:4:

Met Leu Lys Lys Tyr Gln Pro Phe Asp Leu Arg Lys Ile Asn Glu Gly
 1               5                  10                  15
His Ser Ser Asn Ala Lys Leu Val Leu His Ser Glu Ala Cys Asn Ile
                20                  25                  30
Asp Ala Lys Ile Ser Lys Phe Phe Cys Ser Gln Asp Asp Ile Asn Leu
                35                  40                  45
Glu Asn Phe Ile Ala Thr Phe Thr Asp Asn Tyr Lys Ala Pro Glu Val
            50                  55                  60
Tyr Thr Ala Ile Leu Lys Asn Cys Cys Ile Thr Pro Arg Ala Pro Lys
65                  70                  75                  80
Leu Pro Arg (2) INFORMATION FOR SEQ ID NO:5:

(i) SEQUENCE CHARACTERISTICS:
         (A) LENGTH: 3150 base pairs
         (B) TYPE: nucleic acid
         (C) STRANDEDNESS: single
         (D) TOPOLOGY: linear (ix) FEATURE:
         (A) NAME/KEY: CDS
         (B) LOCATION: 376..1557

(ix) FEATURE:
         (A) NAME/KEY: CDS
```

(B) LOCATION: 1586..2740

(ix) FEATURE:
(A) NAME/KEY: CDS
(B) LOCATION: 2743..3150

(xi) SEQUENCE DESCRIPTION: SEQ ID NO:5:

| | |
|---|---|
| CTAGACATTA CATGATTAAT TATAGGACGA GTCATTATGC TAGACATTAA AAATACTCCT | 60 |
| GAAATACGAA TACGTTATGG AGTTACCCTA GATAGTTGAT AAATTTTTCA TCGGAATTTC | 120 |
| ATAAATATAA ATGAGAAATT TATCAACTAT CTAGGGAAAA CTCCGTATTT TATATGGCTT | 180 |
| TTAAATTATA ATGTTTATCT GTATAACGCC CCTCTTGATT TACTTTTTTT TAAAAAAAAT | 240 |
| ACATTTTTTA ATTTGTTTGT AAATTTCTTA TATTTAATTT CTCTTGATTA GGTAACTTAT | 300 |
| TAAAATCAAT CTTTATGTGG ATTTTAAGAC ATACCTATAT AGTTGTTATT CCTTAATATA | 360 |

```
TTGAAGAGAA ATTAG ATG AAA CTC ATC AAA CTT AGA TTA CTC CTT TCT TTG      411
              Met Lys Leu Ile Lys Leu Arg Leu Leu Leu Ser Leu
                1               5                   10

GGG CTG GTT GCT AGT TTG GCT GCC TGC TCA AGC TTA CCC ACT TCA GGC       459
Gly Leu Val Ala Ser Leu Ala Ala Cys Ser Ser Leu Pro Thr Ser Gly
         15                  20                  25

CCT AGC CAT AGT GCG ATT TTA GAG GCT AAT TCC CAG AAC TCA GAT AAA       507
Pro Ser His Ser Ala Ile Leu Glu Ala Asn Ser Gln Asn Ser Asp Lys
     30                  35                  40

CCT TTA CCG GAA GTT AAT TTA GTG GAG TTA GAT AAT GGC TTA GTT CAG       555
Pro Leu Pro Glu Val Asn Leu Val Glu Leu Asp Asn Gly Leu Val Gln
 45                  50                  55                  60

CAG TTG TAT CAG ACT CAG CAA AGT CAG CAA TTT TCC GGC TTT TTA GGC       603
Gln Leu Tyr Gln Thr Gln Gln Ser Gln Gln Phe Ser Gly Phe Leu Gly
             65                  70                  75

ACG GCT GGC GGT GCT GGA TAT GCC GGT GCG GTC AAT GTG GGG GAT GTT       651
Thr Ala Gly Gly Ala Gly Tyr Ala Gly Ala Val Asn Val Gly Asp Val
         80                  85                  90

CTT GAA ATT TCA ATT TGG GAA GCG CCA CCG GCA GTG TTG TTT GGC GGT       699
Leu Glu Ile Ser Ile Trp Glu Ala Pro Pro Ala Val Leu Phe Gly Gly
     95                 100                 105

ACT TTT AGT TCT GAA GGG CAA GGT AGC GGG CAT TTA ACG CAA TTA CCG       747
Thr Phe Ser Ser Glu Gly Gln Gly Ser Gly His Leu Thr Gln Leu Pro
110                 115                 120

GCG CAA ATG GTT AAC CAA AAC GGT ACG GTT ACT GTG CCG TTT GTG GGT       795
Ala Gln Met Val Asn Gln Asn Gly Thr Val Thr Val Pro Phe Val Gly
125                 130                 135                 140

AAT ATT CGT GTT GCA GGT AAA ACA CCG GAA GCG ATT CAG TCT CAA ATT       843
Asn Ile Arg Val Ala Gly Lys Thr Pro Glu Ala Ile Gln Ser Gln Ile
             145                 150                 155

GTT GGG GCA TTG CAA CGT AAA GCG AAT CAG CCA CAA GTA TTA GTA AAA       891
Val Gly Ala Leu Gln Arg Lys Ala Asn Gln Pro Gln Val Leu Val Lys
         160                 165                 170

ATT GCG AAT AAT AAC TCT GCG GAT GTT ACG GTT ATT CGT CAG GGT AAC       939
Ile Ala Asn Asn Asn Ser Ala Asp Val Thr Val Ile Arg Gln Gly Asn
     175                 180                 185

AGT ATT CGT ATG CCG CTG AGT GCG AAT AAC GAA CGT GTG TTA GAT GCT       987
Ser Ile Arg Met Pro Leu Ser Ala Asn Asn Glu Arg Val Leu Asp Ala
190                 195                 200

GTT GCA GCA GTA GGC GGT ACA ACT GAA AAT ATT GAA GAC GTT ACC GTA      1035
Val Ala Ala Val Gly Gly Thr Thr Glu Asn Ile Glu Asp Val Thr Val
205                 210                 215                 220

AAA TTA ACT CGT GGC TCG CAA GTC AAA ACA TTA GCG TTT GAA ACT CTA      1083
Lys Leu Thr Arg Gly Ser Gln Val Lys Thr Leu Ala Phe Glu Thr Leu
                225                 230                 235
```

```
ATT TCC GAT CCG GCG CAA AAT ATT ATG TTA CGT GCC GGC GAT GTC GTT      1131
Ile Ser Asp Pro Ala Gln Asn Ile Met Leu Arg Ala Gly Asp Val Val
        240                 245                 250

TCG TTG CTA AAC ACG CCT TAT AGC TTT ACC GGT TTA GGT GCG GTG GGT      1179
Ser Leu Leu Asn Thr Pro Tyr Ser Phe Thr Gly Leu Gly Ala Val Gly
            255                 260                 265

AAC AAC CAG CAA ATG AAA TTC TCA AGT AAA GGA ATT ACG CTT GCC GAA      1227
Asn Asn Gln Gln Met Lys Phe Ser Ser Lys Gly Ile Thr Leu Ala Glu
        270                 275                 280

GCT ATC GGT AAG ATG GGT GGC CTA ATT GAT ACT CGT TCG GAT CCG AGA      1275
Ala Ile Gly Lys Met Gly Gly Leu Ile Asp Thr Arg Ser Asp Pro Arg
285                 290                 295                 300

GGG GTA TTC GTC TTC CGT CAT GTG CCT TTT TCT CAA TTA AGT TTA GAT      1323
Gly Val Phe Val Phe Arg His Val Pro Phe Ser Gln Leu Ser Leu Asp
            305                 310                 315

CAG CAA ACA CAA TGG GGA GCG AAA GGC TAT GGT ATG GGT ATG GAT GTA      1371
Gln Gln Thr Gln Trp Gly Ala Lys Gly Tyr Gly Met Gly Met Asp Val
        320                 325                 330

CCG ACG GTT TAT CGT GTG AAT TTA CTT GAG CCG CAA TCA CTG TTT TTA      1419
Pro Thr Val Tyr Arg Val Asn Leu Leu Glu Pro Gln Ser Leu Phe Leu
            335                 340                 345

TTA CAA CGC TTC CCG ATG CAA GAT AAA GAT ATT GTC TAT GTA TCA AAT      1467
Leu Gln Arg Phe Pro Met Gln Asp Lys Asp Ile Val Tyr Val Ser Asn
        350                 355                 360

GCA CCG TTG TCC GAA TTC CAA AAA TTC TTG AGA ATG ATT TTC TCG ATT      1515
Ala Pro Leu Ser Glu Phe Gln Lys Phe Leu Arg Met Ile Phe Ser Ile
365                 370                 375                 380

ACT TCG CCG GTT ACA AGT ACG ACT AAT GCT ATT CGT GCC TAT              1557
Thr Ser Pro Val Thr Ser Thr Thr Asn Ala Ile Arg Ala Tyr
            385                 390

TAATATATTG AATTTATAAG GATAAAAAT ATG GAA ACA ACT ATT ACG GCA AGT      1609
                                Met Glu Thr Thr Ile Thr Ala Ser
                                 1               5

CCG ACA GAA AAA CTA CAA AAA CCG GTT AAA CAG AAA AAA AGT TGG TTA      1657
Pro Thr Glu Lys Leu Gln Lys Pro Val Lys Gln Lys Lys Ser Trp Leu
        10                  15                  20

AAA AAG CTT AAT CCG TTA TTT TGG GTA ACT GTA GCG ATT CCT ACG GTA      1705
Lys Lys Leu Asn Pro Leu Phe Trp Val Thr Val Ala Ile Pro Thr Val
25                  30                  35                  40

TTA TCA GCC TTT TAT TTC GGT TCT GTT GCT TCC GAT ATT TAT ATT TCG      1753
Leu Ser Ala Phe Tyr Phe Gly Ser Val Ala Ser Asp Ile Tyr Ile Ser
                45                  50                  55

GAA TCA AGC TTC GTT GTA AGA TCT CCT CAA AAT CAG ACC GCT TTA ACC      1801
Glu Ser Ser Phe Val Val Arg Ser Pro Gln Asn Gln Thr Ala Leu Thr
            60                  65                  70

GGT GTC GGT GCC TTA TTA CAA GGT TCC GGA TTT TCT CGA GCT CAA GAT      1849
Gly Val Gly Ala Leu Leu Gln Gly Ser Gly Phe Ser Arg Ala Gln Asp
        75                  80                  85

GAT ACT TAT ACC GTA CAA GAA TAT ATG CAT TCT CGT ACG GCA CTA GAA      1897
Asp Thr Tyr Thr Val Gln Glu Tyr Met His Ser Arg Thr Ala Leu Glu
        90                  95                  100

CAG TTA ATG AAA GAC TTG CCA ATA CGT GAA TAC TAT GAG AAT CAA GGC      1945
Gln Leu Met Lys Asp Leu Pro Ile Arg Glu Tyr Tyr Glu Asn Gln Gly
105                 110                 115                 120

GAT ATT ATC GCT CGC TTT AAT GGA TTT GGT TTA AAT AAT AGT AAA GAA      1993
Asp Ile Ile Ala Arg Phe Asn Gly Phe Gly Leu Asn Asn Ser Lys Glu
                125                 130                 135

GCG TTT TAT AAA TAT TTC CGA GAT CGC TTA AGT GTG GAC TTT GAC TCT      2041
Ala Phe Tyr Lys Tyr Phe Arg Asp Arg Leu Ser Val Asp Phe Asp Ser
```

-continued

```
            140                 145                 150
GTT TCC GGT ATC GCC AGC TTA CGT ATT CGA GCA TTT AAC GCG GAA GAG     2089
Val Ser Gly Ile Ala Ser Leu Arg Ile Arg Ala Phe Asn Ala Glu Glu
        155                 160                 165

GGG CAA CAA ATT AAT CAA AAA TTA CTT GCC GAA GGT GAA ACG CTT ATT     2137
Gly Gln Gln Ile Asn Gln Lys Leu Leu Ala Glu Gly Glu Thr Leu Ile
    170                 175                 180

AAC CGT TTA AAC GAA CGT GCA AGA AAA GAT ACC ATT TCA TTT GCG GAA     2185
Asn Arg Leu Asn Glu Arg Ala Arg Lys Asp Thr Ile Ser Phe Ala Glu
185                 190                 195                 200

CAA GCG GTT ACA GAA GCG GAA AAT AAT GTA AAC GAA ACG GCA AAT GCT     2233
Gln Ala Val Thr Glu Ala Glu Asn Asn Val Asn Glu Thr Ala Asn Ala
                205                 210                 215

TTA AGT AAA TAC CGT ATC AAA AAT AAA ATC TTT GAT TTA CCG GCA CAA     2281
Leu Ser Lys Tyr Arg Ile Lys Asn Lys Ile Phe Asp Leu Pro Ala Gln
        220                 225                 230

TCC GGC GTA CAA CTT TCA TTA ATT TCC AGC CTA AAA AGC GAA TTG ATT     2329
Ser Gly Val Gln Leu Ser Leu Ile Ser Ser Leu Lys Ser Glu Leu Ile
        235                 240                 245

CGT GTA GAA ACA CAA TTG GCT CAA TTG CAA TCT ATT ACA CCG GAC AAC     2377
Arg Val Glu Thr Gln Leu Ala Gln Leu Gln Ser Ile Thr Pro Asp Asn
    250                 255                 260

CCA CAA GTT GAT GCA TTG CTT ATG CGC CAA AAA AGT TTA CGT AAG GAA     2425
Pro Gln Val Asp Ala Leu Leu Met Arg Gln Lys Ser Leu Arg Lys Glu
265                 270                 275                 280

ATC GAT GAG CAA TCA AAA CAG CTT TCC AGT AAC AGT AAT AGC TCT ATT     2473
Ile Asp Glu Gln Ser Lys Gln Leu Ser Ser Asn Ser Asn Ser Ser Ile
                285                 290                 295

GCT ATT CAA ACT GCC GAT TAC CAA CGC TTA GTA CTT GCA AAC GAG CTG     2521
Ala Ile Gln Thr Ala Asp Tyr Gln Arg Leu Val Leu Ala Asn Glu Leu
        300                 305                 310

GCA CAG CAA CAA TTG ACC GCA GCA TTA ACC TCA TTA CAA AAT ACG AAA     2569
Ala Gln Gln Gln Leu Thr Ala Ala Leu Thr Ser Leu Gln Asn Thr Lys
        315                 320                 325

AAT GAA GCG GAT CGC CAG CAA CTT TAT TTA GAA GTA ATC AGT CAG CCA     2617
Asn Glu Ala Asp Arg Gln Gln Leu Tyr Leu Glu Val Ile Ser Gln Pro
330                 335                 340

AGC AAA CCG GAC TGG GCG GAA GAG CCT TAT CGC TTA TAT AAT ATT TTA     2665
Ser Lys Pro Asp Trp Ala Glu Glu Pro Tyr Arg Leu Tyr Asn Ile Leu
345                 350                 355                 360

GCG ACA TTC TTT ATC GGT CTG ATG CTT TAT GGT GTA TTA AGT TTA TTA     2713
Ala Thr Phe Phe Ile Gly Leu Met Leu Tyr Gly Val Leu Ser Leu Leu
                365                 370                 375

ATT GCA AGC GTA AGA GAG CAC AAA AAC TA ATG CAA TAC GGT GAT CAA      2760
Ile Ala Ser Val Arg Glu His Lys Asn    Met Gln Tyr Gly Asp Gln
        380                 385          1                   5

ACA ACT TTC CGC CAA TCT CTC GCC ATT CAA GGG AGA GTA ATC GGT GCA     2808
Thr Thr Phe Arg Gln Ser Leu Ala Ile Gln Gly Arg Val Ile Gly Ala
            10                  15                  20

TTA CTC ATG CGG GAA ATT ATT ACG CGT TAC GGA CGA AAA AAT TTG GGT     2856
Leu Leu Met Arg Glu Ile Ile Thr Arg Tyr Gly Arg Lys Asn Leu Gly
        25                  30                  35

TTT TTA TGG CTG TTT GTT GAG CCG CTA TTA CTC ACT TTA TTT ATC GTT     2904
Phe Leu Trp Leu Phe Val Glu Pro Leu Leu Leu Thr Leu Phe Ile Val
    40                  45                  50

TTG ATG TGG AAA TTT ATC CGA GCG GAT CGC GTT TCC GAT TTA AAT ATT     2952
Leu Met Trp Lys Phe Ile Arg Ala Asp Arg Val Ser Asp Leu Asn Ile
55                  60                  65                  70

ATT GCT TTT GTG ATT ACC GGT TAT CCA ATG GCC ATG ATG TGG CGT AAT     3000
```

```
Ile Ala Phe Val Ile Thr Gly Tyr Pro Met Ala Met Met Trp Arg Asn
                75                  80                  85

GCG TCA AAC CGC ACT ATC GGT GCA ATT TCC GGT AAC TTG AGT CTT CTT      3048
Ala Ser Asn Arg Thr Ile Gly Ala Ile Ser Gly Asn Leu Ser Leu Leu
            90                  95                 100

TAT CAT CGT AAT GTT CGC GTA TTA GAT ACC TTA CTG GCT CGT GTC ATA      3096
Tyr His Arg Asn Val Arg Val Leu Asp Thr Leu Leu Ala Arg Val Ile
       105                 110                 115

CTT GAA GTA GCA GGT GCA ACG ATT GCC CAA ATC ATT ATT ATG GCA TTA      3144
Leu Glu Val Ala Gly Ala Thr Ile Ala Gln Ile Ile Ile Met Ala Leu
   120                 125                 130

GTC ATT                                                              3150
Val Ile
135
```

(2) INFORMATION FOR SEQ ID NO:6:

(i) SEQUENCE CHARACTERISTICS:
        (A) LENGTH: 394 amino acids
        (B) TYPE: amino acid
        (D) TOPOLOGY: linear (ii) MOLECULE TYPE: protein (xi) SEQUENCE DESCRIPTION: SEQ ID NO:6:

```
Met Lys Leu Ile Lys Leu Arg Leu Leu Leu Ser Leu Gly Leu Val Ala
 1               5                  10                  15

Ser Leu Ala Ala Cys Ser Ser Leu Pro Thr Ser Gly Pro Ser His Ser
            20                  25                  30

Ala Ile Leu Glu Ala Asn Ser Gln Asn Ser Asp Lys Pro Leu Pro Glu
        35                  40                  45

Val Asn Leu Val Glu Leu Asp Asn Gly Leu Val Gln Gln Leu Tyr Gln
    50                  55                  60

Thr Gln Gln Ser Gln Gln Phe Ser Gly Phe Leu Gly Thr Ala Gly Gly
 65                  70                  75                  80

Ala Gly Tyr Ala Gly Ala Val Asn Val Gly Asp Val Leu Glu Ile Ser
                85                  90                  95

Ile Trp Glu Ala Pro Pro Ala Val Leu Phe Gly Gly Thr Phe Ser Ser
            100                 105                 110

Glu Gly Gln Gly Ser Gly His Leu Thr Gln Leu Pro Ala Gln Met Val
        115                 120                 125

Asn Gln Asn Gly Thr Val Thr Val Pro Phe Val Gly Asn Ile Arg Val
    130                 135                 140

Ala Gly Lys Thr Pro Glu Ala Ile Gln Ser Gln Ile Val Gly Ala Leu
145                 150                 155                 160

Gln Arg Lys Ala Asn Gln Pro Gln Val Leu Val Lys Ile Ala Asn Asn
                165                 170                 175

Asn Ser Ala Asp Val Thr Val Ile Arg Gln Gly Asn Ser Ile Arg Met
            180                 185                 190

Pro Leu Ser Ala Asn Asn Glu Arg Val Leu Asp Ala Val Ala Ala Val
        195                 200                 205

Gly Gly Thr Thr Glu Asn Ile Glu Asp Val Thr Val Lys Leu Thr Arg
    210                 215                 220

Gly Ser Gln Val Lys Thr Leu Ala Phe Glu Thr Leu Ile Ser Asp Pro
225                 230                 235                 240

Ala Gln Asn Ile Met Leu Arg Ala Gly Asp Val Val Ser Leu Leu Asn
                245                 250                 255
```

```
Thr Pro Tyr Ser Phe Thr Gly Leu Gly Ala Val Gly Asn Asn Gln Gln
            260                 265                 270

Met Lys Phe Ser Ser Lys Gly Ile Thr Leu Ala Glu Ala Ile Gly Lys
        275                 280                 285

Met Gly Gly Leu Ile Asp Thr Arg Ser Asp Pro Arg Gly Val Phe Val
        290                 295                 300

Phe Arg His Val Pro Phe Ser Gln Leu Ser Leu Asp Gln Gln Thr Gln
305                 310                 315                 320

Trp Gly Ala Lys Gly Tyr Gly Met Gly Met Asp Val Pro Thr Val Tyr
                325                 330                 335

Arg Val Asn Leu Leu Glu Pro Gln Ser Leu Phe Leu Leu Gln Arg Phe
            340                 345                 350

Pro Met Gln Asp Lys Asp Ile Val Tyr Val Ser Asn Ala Pro Leu Ser
        355                 360                 365

Glu Phe Gln Lys Phe Leu Arg Met Ile Phe Ser Ile Thr Ser Pro Val
370                 375                 380

Thr Ser Thr Thr Asn Ala Ile Arg Ala Tyr
385                 390

(2) INFORMATION FOR SEQ ID NO:7:

(i) SEQUENCE CHARACTERISTICS:
        (A) LENGTH: 385 amino acids
        (B) TYPE: amino acid
        (D) TOPOLOGY: linear (ii) MOLECULE TYPE: protein (xi) SEQUENCE DESCRIPTION: SEQ ID NO:7:

Met Glu Thr Thr Ile Thr Ala Ser Pro Thr Glu Lys Leu Gln Lys Pro
1               5                   10                  15

Val Lys Gln Lys Lys Ser Trp Leu Lys Lys Leu Asn Pro Leu Phe Trp
            20                  25                  30

Val Thr Val Ala Ile Pro Thr Val Leu Ser Ala Phe Tyr Phe Gly Ser
        35                  40                  45

Val Ala Ser Asp Ile Tyr Ile Ser Glu Ser Ser Phe Val Val Arg Ser
    50                  55                  60

Pro Gln Asn Gln Thr Ala Leu Thr Gly Val Gly Ala Leu Leu Gln Gly
65                  70                  75                  80

Ser Gly Phe Ser Arg Ala Gln Asp Asp Thr Tyr Thr Val Gln Glu Tyr
                85                  90                  95

Met His Ser Arg Thr Ala Leu Glu Gln Leu Met Lys Asp Leu Pro Ile
            100                 105                 110

Arg Glu Tyr Tyr Glu Asn Gln Gly Asp Ile Ile Ala Arg Phe Asn Gly
        115                 120                 125

Phe Gly Leu Asn Asn Ser Lys Glu Ala Phe Tyr Lys Tyr Phe Arg Asp
    130                 135                 140

Arg Leu Ser Val Asp Phe Asp Ser Val Ser Gly Ile Ala Ser Leu Arg
145                 150                 155                 160

Ile Arg Ala Phe Asn Ala Glu Glu Gly Gln Gln Ile Asn Gln Lys Leu
                165                 170                 175

Leu Ala Glu Gly Glu Thr Leu Ile Asn Arg Leu Asn Glu Arg Ala Arg
            180                 185                 190

Lys Asp Thr Ile Ser Phe Ala Glu Gln Ala Val Thr Glu Ala Glu Asn
        195                 200                 205

Asn Val Asn Glu Thr Ala Asn Ala Leu Ser Lys Tyr Arg Ile Lys Asn
```

```
              210                 215                 220
Lys Ile Phe Asp Leu Pro Ala Gln Ser Gly Val Gln Leu Ser Leu Ile
225                 230                 235                 240

Ser Ser Leu Lys Ser Glu Leu Ile Arg Val Glu Thr Gln Leu Ala Gln
                245                 250                 255

Leu Gln Ser Ile Thr Pro Asp Asn Pro Gln Val Asp Ala Leu Leu Met
                260                 265                 270

Arg Gln Lys Ser Leu Arg Lys Glu Ile Asp Glu Gln Ser Lys Gln Leu
                275                 280                 285

Ser Ser Asn Ser Asn Ser Ser Ile Ala Ile Gln Thr Ala Asp Tyr Gln
290                 295                 300

Arg Leu Val Leu Ala Asn Glu Leu Ala Gln Gln Gln Leu Thr Ala Ala
305                 310                 315                 320

Leu Thr Ser Leu Gln Asn Thr Lys Asn Glu Ala Asp Arg Gln Gln Leu
                325                 330                 335

Tyr Leu Glu Val Ile Ser Gln Pro Ser Lys Pro Asp Trp Ala Glu Glu
                340                 345                 350

Pro Tyr Arg Leu Tyr Asn Ile Leu Ala Thr Phe Phe Ile Gly Leu Met
                355                 360                 365

Leu Tyr Gly Val Leu Ser Leu Leu Ile Ala Ser Val Arg Glu His Lys
370                 375                 380

Asn
385

(2) INFORMATION FOR SEQ ID NO:8:

(i) SEQUENCE CHARACTERISTICS:
         (A) LENGTH: 136 amino acids
         (B) TYPE: amino acid
         (D) TOPOLOGY: linear (ii) MOLECULE TYPE: protein (xi) SEQUENCE DESCRIPTION: SEQ ID NO:8:

Met Gln Tyr Gly Asp Gln Thr Thr Phe Arg Gln Ser Leu Ala Ile Gln
1               5                   10                  15

Gly Arg Val Ile Gly Ala Leu Leu Met Arg Glu Ile Ile Thr Arg Tyr
                20                  25                  30

Gly Arg Lys Asn Leu Gly Phe Leu Trp Leu Phe Val Glu Pro Leu Leu
                35                  40                  45

Leu Thr Leu Phe Ile Val Leu Met Trp Lys Phe Ile Arg Ala Asp Arg
            50                  55                  60

Val Ser Asp Leu Asn Ile Ile Ala Phe Val Ile Thr Gly Tyr Pro Met
65                  70                  75                  80

Ala Met Met Trp Arg Asn Ala Ser Asn Arg Thr Ile Gly Ala Ile Ser
                85                  90                  95

Gly Asn Leu Ser Leu Leu Tyr His Arg Asn Val Arg Val Leu Asp Thr
                100                 105                 110

Leu Leu Ala Arg Val Ile Leu Glu Val Ala Gly Ala Thr Ile Ala Gln
                115                 120                 125

Ile Ile Ile Met Ala Leu Val Ile
130                 135
```

RECOMBINANT VACCINE FOR DISEASES CAUSED BY ENCAPSULATED ORGANISMS

BACKGROUND OF THE INVENTION

1. Field of the Invention

The invention relates generally to vaccines used in veterinary applications and, more particularly, to a live, recombinant, attenuated vaccine for disease states that are caused by organisms that include capsule where the presence of the capsule is required for virulence but not immunoprotection. The invention has specific application to a recombinantly produced vaccine that has been engineered such that it lacks capsule.

2. Description of the Prior Art

Vaccines are preparations used to prevent specific diseases in animals and humans by inducing immunity. This is accomplished by exposing a patient to an antigen for a particular disease which, in turn, causes the immune system of the patient to produce large quantities of antibody. The presence of the antibody in the patient's blood protects the patient from a later attack by the disease causing agent. Vaccines may either be composed of subunits of the agent, or the live or killed agent itself. For example, poliomyelitis, commonly referred to as "polio", is typically prevented by either administering a live, attenuated oral poliovirus vaccine, which is common practice for treating children, or by administering a killed or inactivated poliovirus vaccine, which is the usual practice for treating adults since they are generally at higher risk for contracting polio from the live vaccine. If a live vaccine is to be used, its virulence must be attenuated in some way; otherwise the virus in the vaccine will cause the disease it is intended to protect against.

A number of diseases are caused by encapsulated bacteria wherein the capsule, which is the gum-like layer of polysacharide or polypeptide exterior to the cell wall of these bacteria, is required for pathogenesis. Swine pleuropneumonia is one example, and virulence factors for *Actinobacillus pleuropneumoniae*, the bacterium which causes the disease, include capsular polysaccharide, endotoxin, and protein exotoxins. Swine pleuropneumonia is one of the major respiratory diseases affecting swine production throughout the world, and accounts for millions of dollars in annual losses to the industry in the United States alone.

U.S. Pat. No. 5,429,818 to Inzana, which is herein incorporated by reference, discloses that non-encapsulated mutants of *Actinobacillus pleuropneumoniae* are avirulent and capable of providing excellent protection against subsequent exposure to the virulent bacteria. The non-capsulated mutants described in Inzana were prepared by ethylmethanesulfunate mutagenesis. However, such procedures have the disadvantages that some spontaneous or chemically induced mutants may not be stable, and the nature of the mutation(s) is (are) unknown.

SUMMARY OF THE INVENTION

It is an object of this invention to provide a safe and effective, live, attenuated, recombinant vaccine for diseases caused by bacteria and fungi which are normally encapsulated and where the capsule is required for virulence but not immunoprotection.

It is another object of this invention to genetically engineer certain bacteria or fungi to lack capsule such that they are rendered avirulent and the genetic nature of the mutation is known.

It is yet another object of this invention to provide a safe and effective, live, attenuated, recombinant vaccine for pleuropneumonia.

According to the invention, a recombinant, live, attenuated strain of *Actinobacillus pleuropneumoniae* which has been genetically engineered to lack capsule has been produced. Since the capsule is required for virulence, but not immunoprotection, the strain will be useful as a vaccine against swine pleuropneumonia. The vaccine was produced by cloned plasmid vector that cannot replicate in *A. pleuropneumoniae*. The capsule export and synthesis genes of *A. pleuropneumoniae* serotype 5 were sequenced. A large deletion was made in the cloned synthesis genes for the capsule, and genes encoding for kanamycin resistance and sucrose sensitivity were then cloned into the deleted site to serve as marker genes. This suicide vector was inserted into a virulent *A. pleuropneumoniae* serotype 5 strain using electroporation in order to obtain a homologous recombination event by double cross over between homologous regions of the chromosome and plasmid. Four isolates were obtained, and each lacked iridescence suggesting a lack of capsule. The lack of capsule and the deleted region of the capsule genes was confirmed in one strain by dot blotting and Southern blotting, respectively. The presence of the marker genes in the recombinant strain was also confirmed. No other change in any other phenotypic properties could be identified, and the marker genes were not found in other regions of the chromosome. The recombinant strain, referred to as J45-100, was very serum sensitive, had reduced virulence in pigs at ten times the 50% lethal dose for the parent strain, and should provide protection for swine against pleuropneumonia.

This invention will be useful for producing vaccines against any encapsulated organism that produces toxins or other virulence factors where the capsule is required for virulence but not immunoprotection. All that will be required will be to clone the genes encoding for capsule synthesis for the organism, and then delete and replace the section of the cloned gene with a marker gene on a suicide vector, and then introduce the vector into the desired organism and screen for a genetically modified organism that lacks capsule. The invention should be useful in producing vaccines for additional bacteria infectants including, but not limited to, *Pasteurella multocida, Pasteurella haemolytica*, and *Pseudomonas aeruginosa*, as well as fungi such as *Cryptococcus neoformans* which is a pathogen associated with acquired immune deficiency syndrome (AIDS) in cats and humans.

BRIEF DESCRIPTION OF THE DRAWINGS

The foregoing and other objects, aspects and advantages will be better understood from the following detailed description of the preferred embodiments of the invention with reference to the drawings, in which:

FIGS. 3a and 3b present the nucleotide sequence of the 3.2 kb HindIII-EcoRV fragment of pCW-11E, containing the serotype-specific A. pleuropneumoniae J45 DNA (SEQ ID NO. 1). The deduced amino acid sequences of the two complete ORFs detected in this sequence, cpsA (SEQ ID NO.2) and cpsB (SEQ ID NO.3), and the deduced N-terminal sequence of a third incomplete ORF, cpsC (SEQ ID NO. 4), are indicated below the nucleotide sequence. Putative ribosome-binding sites preceding each ORF are in boldface, and putative −10 and −35 promoter sequences upstream from cpsA are indicated.

FIGS. 10a and 10b present the nucleotide sequence of the 3.2 kb XbaI-ClaI fragment of pCW-1C encoding for the capsule export genes of A. pleuropneumoniae J45 DNA (SEQ ID NO. 5). The deduced amino acid sequences (SEQ ID Nos. 6–9) of proteins involved in the export of the A. pleuropneumoniae serotype 5a capsular polysacharide are presented.

DETAILED DESCRIPTION OF THE PREFERRED EMBODIMENTS OF THE INVENTION

Figure 1:
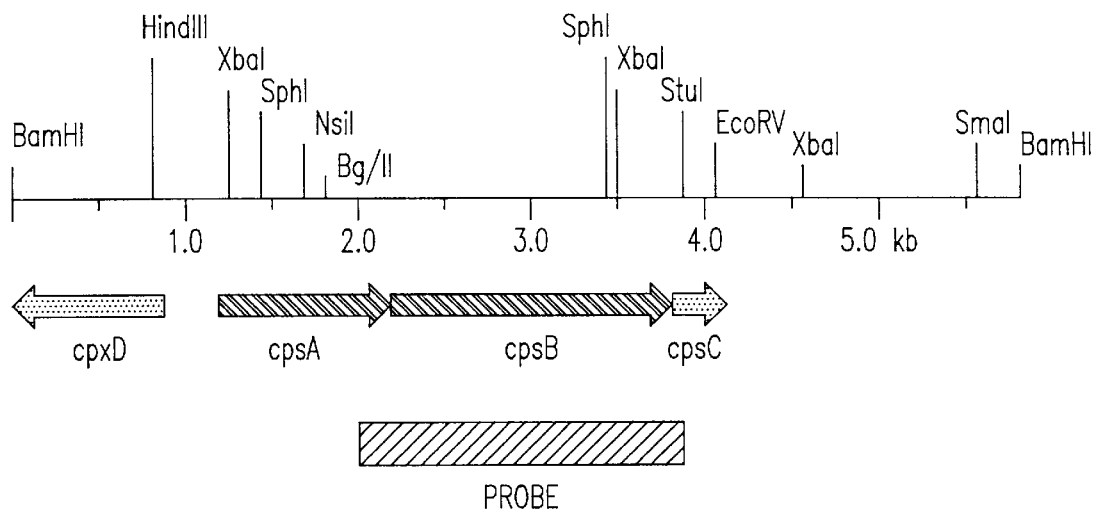
FIG. 1 is a physical map of pCW-11 E cloned DNA from the capsule synthesis region of *A. pleuropneumoniae* J45. The location and direction of transcription of the two complete ORFs (cpsA and cpsB, solid fill) identified by dideoxy sequencing is indicated. The location of a partial third potential ORF (cpsC) is also indicated. The location and direction of transcription of the incomplete capsule export gene cpxD located on this DNA fragment is also indicated. The 2.1 kb BglII-StuI fragment used as the DNA probe in FIG. 2 is indicated. Dotted fill indicates incomplete ORFs.

The invention contemplates using a live, recombinantly produced, avirulent, strain of a microorganism (i.e., bacteria or fungus) which has been genetically engineered to be non-capsulated as a vaccine against diseases caused by the microorganism. The invention will have utility in preventing diseases wherein the capsule of the microorganism is required for virulence but not immunoprotection, and where the disease is caused by toxins or other virulence factors. As a particular example of the invention, a non-capsulated strain of Actinobacillus pleuropneumoniae has been produced and should be useful as a vaccine against pleuropneumonia in swine. The chief feature of the invention is the genetic modification of the microorganism, which, in a specific embodiment is Actinobacillus pleuropneumoniae, to include a deletion in its deoxyribonucleic acid (DNA) in the region encoding for capsule synthesis. For exemplary purposes only, the synthesis of a transformed Actinobacillus pleuropneumoniae serotype 5 mutant is disclosed; however, it should be understood that other serotypes could be prepared in a manner similar to that which is described below, and would be useful in a vaccine alone or in combination with one or more recombinant mutants of different serotypes.

The strain described below, along with other strains of noncapsulated, toxigenic bacteria or other microorganisms generated according to the procedures described below, will make excellent vaccines because they are avirulent, but produce all the antigens necessary for the host to make a protective immune response. The vaccines can be administered by a variety of methods; however, intramuscular or subcutaneous injection is preferred. The advantage of these live vaccines is that the toxins that are primarily responsible for the disease and other components only made by live organisms or in vivo, will be made at the immunization site and the host will make an immune response which protects itself from the lesions caused by the toxins. Hence, the disease (acute or chronic) does not occur. The organisms cannot disseminate, however, because without capsule, they are extremely serum sensitive, and are cleared immediately in the bloodstream or respiratory tract. In addition, as a live vaccine, the cell-mediated immune response will be greater and the protection will last longer than with killed vaccines.

EXAMPLE

A DNA region involved in Actinobacillus pleuropneumoniae capsular polysaccharide biosynthesis was identified and characterized. A probe specific for the cpxD gene involved in the export of the *A. pleuropneumoniae* serotype 5a J45 capsular polysaccharide was used to identify and clone an adjacent 5.8 kilobase BamHI fragment of J45 genomic DNA. Southern blot analyses demonstrated that a portion of this region contained DNA that was serotype-specific. DNA sequence analysis demonstrated that this region contained two complete open reading frames, cpsA and cpsB, and an incomplete potential third open reading frame, cpsC. cpsA and cpsB shared some low homology with glycosyltransferases involved in the biosynthesis of *Escherichia coli* lipopolysaccharide and *Haemophilus influenzae* type b capsular polysaccharide, respectively. A 2.1 kilobase deletion which spanned the cloned cpsABC open reading frames was constructed and recombined into the J45 chromosome by allelic exchange to produce the mutant J45-100. This mutant did not produce intracellular or extracellular capsular polysaccharide, indicating that cpsA, cpsB, and/or cpsC were involved in *A. pleuropneumoniae* capsular polysaccharide biosynthesis. The Apx toxin and lipopolysaccharide profiles of J45-100 were identical to the encapsulated parent strain, J45. However, J45-100 grew faster in vitro than J45. J45-100 was sensitive to killing in precolostral calf serum, whereas J45 was not. J45-100 was avirulent when used to challenge pigs intratracheally with 3 times the 50% lethal dose of strain J45. At 6 times the 50% lethal dose of J45, J345-100 caused mild to moderate lung lesions, but not death. These results demonstrated that the capsular polysaccharide is a major determinant of serum-resistance and virulence of *A. pleuropneumoniae*.

MATERIALS AND METHODS

Bacterial strains, plasmids, and growth conditions. The bacterial strains and plasmfids used in this study are as described in Table 1. For genomic DNA extraction and for bactericidal assays, *A. pleuropneumoniae* strains were grown with shaking at 37° C. in brain heart infusion broth (Difco Laboratories, Detroit, Mich.) containing 5 μg/ml nicotinamide adenine dinucleotide (NAD) (Sigma Chemical Co., St. Louis, Mo.). For electroporation, *A. pleuropneumoniae* strains were grown with shaking at 37° C. in tryptic soy broth (Difco Laboratories) containing 0.6% yeast extract (Difco Laboratories) and 5 μg/ml NAD (TSY-N). For pig challenge experiments, *A. pleuropneumoniae* strains were grown with shaking at 37° C. in Columbia broth (Difco Laboratories) containing 5 μg/ml NAD. *Escherichia coli* strains were grown in Luria-Bertani broth (Sambrook et al., 1989) for routine cultivation, or in Terrific broth (Tartof and Hobbes, 1987) for extraction of plasmids. Antibiotics were used in growth media for maintenance of plasmids in *E. coli* at the following concentrations: ampicillin (Amp) 100 μg/ml, and kanamycin (Kan) 50 μg/ml Kanamycin was used at 85 μg/ml for selection of *A. pleuropneumoniae* recombinant mutants.

TABLE 1

Bacterial strains and plasmids used

| Strain or plasmid | Relevant genotype or characteristics | Source or reference |
|---|---|---|
| *A. pleuropneumoniae* Strains | | |
| 4074 | serotype 1; (ATCC 27088) | ATCC[a] |
| 1536 | serotype 2; (ATCC 27089) | ATCC[a] |
| J45 | serotype 5a | Fenwick et al., 1986a |
| K17 | serotype 5a | Nielsen, 1986a |
| 178 | serotype 5 | M. Mulks |
| 29628 | serotype 7 | L. Hoffman |
| 13261 | serotype 9 | J. Nicolet |
| J45-C | noncapsulated mutant isolated after ethyl methanesulfonate mutagenesis of strain J45 | Inzana et al., 1993a |
| J45-100 | recombinant noncapsulated mutant derived from strain J45 | This chapter |
| *E. coli* Strains | | |
| XL1-Blue | recA1 endA1 gyrA96 thi-1 hsdR17 supE44 relA1 lac ($F^+$ proAB $lacI^qZ\Delta M15$ Tn10); Host for recombinant plasmids | Stratagene, LaJolla, Calif. |
| Plasmids | | |
| pGEM-3Z | Cloning vector, 2.74 kb; $Amp^r$ | Promega |
| pCW-1C | 5.3 kb XbaI fragment of J45 cloned into pGEM-3Z | Chapter 3 |
| pCW-11E | 5.8 kb BamHI fragment of J45 cloned into pGEM-3Z | This work |
| pKS | 3.8 kb BamHI fragment containing the nptl[b]-sacRB cartridge[c] cloned into the BamHI site of pGEM-3Z; $Amp^r$, $Kan^r$ | S. M. Boyle |
| pCW11EΔ1KS1 | pCW-11E with the 2.1 kb BglII-StuI fragment deleted and the 3.8 kbBamHI nptl-sacRB cartridge from pKS ligated in | This chapter |

[a]American Type Culture Collection, Rockville, Md.
[b]This marker was originally derived from the Tn903 nptl gene of pUC4K (Pharmacia Biotech, Piscataway, N.J.).
[c]This cartridge has been previously described (Ried and Collmer, 1987).

Calculation of generation time. The generation time of logarithmic phase *A. pleuropneumoniae* strains grown in TSY-N was calculated using the equation: R=1/g, where R is the average rate of bacterial growth, and g is the generation time of the bacterial population (Pelczar et al., 1993). The average rate of growth, R, was calculated using the following equation: $R=3.32(\log_{10} N - \log_{10} N_0)/t$, where t is the elapsed time, N is the number of bacteria at time=t, and $N_0$ is the initial number of bacteria at time=0 (Pelczar et al., 1993).

DNA hybridization analysis. Restriction endonuclease-digested DNA (approximately 5 μg per lane) was electrophoresed through 0.7% agarose gels and was transferred by capillary action to MagnaGraph nylon membranes (Micron Separations Inc., Westboro, Mass.) using 20× saline sodium citrate (20× SSC is 3 M NaCl, 300 mM sodium citrate, pH 7) as previously described (Sambrook et al., 1989; Southern, 1975). DNA was covalently linked to nylon membranes by ultraviolet irradiation using a UV Stratalinker (Stratagene, La Jolla, Calif.). Digoxigenin-labeled probes for DNA hybridizations were synthesized by the random primer method using the Genius System nonradioactive labeling and detection kit (Boehringer-Mannheim Corp., Indianapolis, Ind.) according to the manufacturer's directions. DNA hybridizations were performed at 68° C. in solutions containing 5×SSC. The membranes were washed and developed according to the Genius System directions for calorimetric detection.

Recombinant DNA methods and reagents. Genomic DNA was isolated from broth-grown A. pleuropneumoniae cells using a method described by S. Spinola. Briefly, bacteria were resuspended in 10 mM Tris-1 mM EDTA (pH 8) and incubated with sodium dodecyl sulfate (0.66%), and RNAse (100 μg/ml) for 1 hour at 37° C. Proteinase K was added to a final concentration of 100 μg/ml, and the mixture was incubated at 56° C. for 1 hour. The mixture was extracted once with buffered phenol and four times with buffered phenol-chloroform (Amresco, Inc., Solon, Ohio), and the genomic DNA was ethanol precipitated and resuspended in 10 mM Tris-1 mM EDTA (pH 8). Plasmid DNA was isolated by a rapid alkaline lysis method (Ish-Horowicz and Burke, 1981). Restriction fragments required for cloning and probe synthesis were eluted from agarose gels as described (Zhen and Swank, 1993). Restriction digests, agarose gel electrophoresis, and DNA ligations were performed as previously described (Sambrook et al., 1989). Restriction fragment ends were made blunt-ended by filling in 5' overhangs with nucleotides (dNTPs) using the Klenow fragment of DNA polymerase 1, as previously described (Sambrook et al., 1989). Plasmid DNA was transformed into E. coli strains by electroporation (Dower et al., 1988) using a BTX ECM 600 electroporator (BTX, Inc., San Diego, Calif.).

Restriction endonucleases and the Klenow fragment of DNA polymerase I were obtained from Promega Corporation (Madison, Wis.). T4 DNA ligase was obtained from Gibco BRL (Gaithersburg, Md.). Nucleotides (dNTPs) for fill-in reactions were obtained from Boehringer-Mannheim Corporation (Indianapolis, Ind.).

DNA sequencing and analysis. The nucleotide sequence of both strands of the 2.7 kilobase (kb) XbaI-EcoRV DNA fragment of pCW-11E was determined by the dideoxy chain-termination method (Sanger et al., 1977) using the Sequenase version 2.0 DNA sequencing kit (United States Biochemical Corp., Cleveland, Ohio) with $\alpha^{35}[S]dATP$ (DuPont/NEN Research Products, Boston, Mass.). Double stranded DNA templates were sequenced using custom, oligonucleotide primers (DNAgency, Inc., Malverne, Pa.) to continue reading along each strand.

The nucleotide sequence obtained was combined with the nucleotide sequence of the 4.6 kb XbaI-ClaI DNA fragment of pCW-1C encoding for the upstream capsule structural genes (FIG. 10), and was analyzed using DNASTAR analysis software (DNASTAR, Inc, Madison, Wis.). Sequence similarity searches of the EMBUGenBank/DDBJ databases were performed using BLAST software (Altschul et al., 1990) at the National Center for Biotechnology Information (Bethesda, Md.).

Conserved regions of the H. influenzae type b cap (capb) locus involved in capsular polysacharide export was used to identify, clone, and characterize a portion of the A. pleuropneumoniae serotype 5a capsulation locus involved in capsular polysacharide export. Southern blot analyses of A. pleuropneumoniae serotype 5a strain J45 genomic DNA with probes specific for contiguous regions of the H. influenzae type b capsulation (capb) locus were performed. These probes did not hybridize to A. pleuropneumoniae genomic DNA under conditions of high stringency (68° C., 5× SSC), but did hybridize under conditions of medium-to-low stringency (55° C., 5× SSC). A 4.4 kb EcoRI fragment of the H. influenzae capb locus from the plasmid pSKH1 containing the region 1 bexD gene involved in capsular polysacharide export and two region 2 open reading frames (ORFs) involved in capsular polysacharide biosynthesis, hybridized to 1.2 kb HindIII and 5.3 kb XbaI fragments of J45 genomic DNA. A 9.0 kb EcoRI fragment of the H. influenzae capb locus from the plasmid pSKH2, containing the region 1 bexCBA genes involved in capsular polysacharide export, some uncharacterized region 3 DNA common to several H. influenzae serotypes, and some region 2 DNA involved in capsular polysaccharide biosynthesis, hybridized to 1.5 kb HindIII, 5.3 kb XbaI, and 2.4 kb XhoI fragments of J45 genomic DNA. These data indicated that the H. influenzae type b and A. pleuropneumoniae serotype 5a capsule gene loci shared homologous regions. The H. influenzae capb specific probes both contain region 1 DNA involved in capsular polysaccharide export, suggesting that the 5.3 XbaI genomic DNA fragment from J45 that hybridized to both H. influenzae capb probes may contain genes that encode proteins involved in export of the A. pleuoropneumoniae serotype 5a capsular polysaccharide. The 5.3 XbaI genomic DNA fragment from J45 that hybridized to the two H. influenzae capb probes was cloned into the XbaI site of the plasmid pGEM-3Z (in both orientations) from XbaI-digested J45 genomic DNA fragments in the range of 4.8 to 6.0 kb that were electroeluted (following electrophoretic separation) from an agaraose gel. One of the resulting plasmids was designated pCW-1C. Southern blots were performed to determine if the H. influenzae type b bexD, bexC, bexB, and bexA hybridized to adjacent fragments of pCW-1C in the same order (bexDCBA) in which these genes occur in H. influenzae. The results suggested that the A. pleuropneumoniae serotype 5a DNA region required for capsular polysaccharide export had been successfully cloned, and that this region was organized in a similar manner to the H. influenzae tybe b bex locus.

Figure 11:
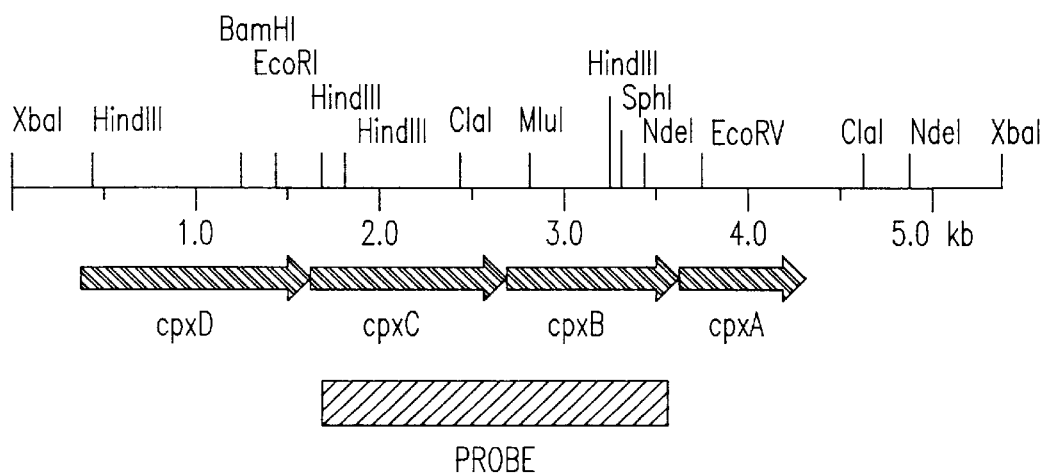
FIG. 11 is a physical map of pCW-1C DNA from A. pleuropneumoniae J45

The nucleotide sequence of the 4.6 kb XbaI-ClaI restriction fragment of pCW-1C was determined and a 3.2 kb XbaI-ClaI restriction fragment is presented in FIGS. 10a–b. Four ORFs (shown in FIGS. 10a–b (SEQ ID NO.5) and FIG. 11) designated cpxDCBA (cpx is used to designate capsular polysaccharide export) were detected in close proximity on the same DNA strand. The AUG initiation codon of cpxC (SEQ ID NO. 7) was 26 nucleotides downstream from the UAA termination codon of cpxD (SEQ ID NO. 6), whereas the AUG initiation codon of cpxB (SEQ ID NO.8) overlapped the UAA termination codon of cpxC (SEQ ID NO.7), and the AUG initiation codon of cpxA (not shown) overlapped the UGA termination codon of cpxB partially present (SEQ ID NO. 8). Shine-Dalgarno ribosome binding consensus sequences were identified within 17 bases upstream of each AUG initiation codon and a putative promoter containing sequences similar to E. coli $\sigma^{70}$-10 (TATAAT) and -35 (TTGACA) consensus sequences was identified upstream of cpxD (SEQ ID NO. 6). A palindromic sequence which may function as a rho-independent transcription termination signal was identified downstream of cpxA (SEQ ID NO. 9). The genetic organization suggests that cpxDCBA are transcribed onto a singel, polycistronic mRNA.

Electrotransformation of A. pleuropneumoniae. A. pleuropneumoniae was grown to midlogarithmic phase in TSY-N, pelleted by centrifugation at 7000×g at 4° C., and washed four times in a chilled (4° C.), filter-sterilized buffer containing 272 mM mannitol, 2.43 mM K2HP04, 0.57 mM KH2P04, 15% glycerol, pH 7.5. This buffer was modified (to contain mannitol in place of sucrose) from a previously described buffer used for washing A. pleuropneumoniae cells prior to electroporation (Lalonde et al., 1989b). The cells were then washed one time in chilled, filter-sterilized 15% glycerol, and resuspended to approximately $10^{10}$ CFU/ml in 15% glycerol. Aliquots of this suspension (90 μl) were mixed with 1.5–2.0 μeg of plasmid DNA (in 1.5 μl distilled water) that had been purified by cesium chloride density gradient ultracentrifugation (Sambrook et al., 1989), placed in chilled 2 mm gap electroporation cuvettes (BTX, Inc.), and electroporated using a BTX ECM 600 electroporator (BTX, Inc.) set to a charging voltage of 2.5 kV and to a resistance setting of R7 (246 ohms). The actual pulse generated was 2.39 kV delivered over 10.7 milliseconds. After electroporation, the cells were recovered in 1 ml TSY-N containing 5 mM $MgCl_2$ with gentle shaking for 3.5 hours at 37° C. After recovery, the cells were cultured on TSY-N agar containing 85 μg of kanamycin per ml and were incubated at 37° C.

Immunoblotting. For colony immunoblots, A. pleuropneumoniae whole cells grown overnight on TSY-N agar plates were scraped into phosphatebuffered saline (PBS) and adjusted to $10^9$ CFU/ml, as determined spectrophotometrically. Approximately $5 \times 10^4$ or $5 \times 10^5$ CFU per well was applied to a nitrocellulose membrane (NitroBind; Micron Separations Inc.) using a Bio-Dot apparatus (Bio-Rad Laboratories, Richmond, Calif.). The membrane was placed in chloroform for 15 minutes at room temperature to lyse the bacterial cells on the membrane. The membrane was air dried completely, and incubated for 1 hour at room temperature in Tris-buffered saline, pH 7.5 (TBS) containing 2% skim milk to block nonspecific binding sites on the membrane. The membrane was incubated for 1 hour at room temperature in a 1:200 dilution (in 2% milk-TBS) of an adsorbed swine antiserum that contained antibodies to the serotype 5a capsular polysaccharide, but not other A. pleuropneumoniae surface antigens. This capsular polysaccharide-enriched antiserum was prepared by adsorbing hyperimmune swine antiserum to A. pleuropneumoniae K17 with a spontaneous noncapsulated mutant, K17-C (Inzana and Mathison, 1987), as described previously (Inzana, 1995). The membrane was washed in TBS containing 0.05% Tween 20, then incubated 1 hour at room temperature in a 1:1000 dilution of rabbit anti-swine IgG conjugated to horseradish peroxidase (heavy and light chains; Cappel, Durham, N.C.). The membrane was washed in TBS, then developed with 4-chloro-1-naphthol (Bio-Rad Laboratories) in TBS containing 0.02% $H_2O_2$.

Immunoblotting of A. pleuropneumoniae concentrated culture supernatants was performed as described previously (Ma and Inzana, 1990). Briefly, approximately 15 μg of total culture supernatant protein was separated by discontinuous SDS-PAGE (Laemmli, 1970) through an 8% separating gel. The proteins were transferred to a nitrocellulose membrane (NitroBind; Micron Separations Inc.) by the method of Towbin et al. (1979). The membrane was incubated in TBS containing 2% bovine serum albumin to block nonspecific binding and was cut into strips. The strips were incubated overnight at 4° C. with either a monoclonal antibody specific for the Apxll toxin (Ma and Inzana, 1990) or a monoclonal antibody specific for the Apxl toxin (Devendish et al., 1989; Frey et al., 1992), and washed in TBS. The blot reacting with the Apxll-specific monoclonal antibody was incubated with a 1:2000 dilution of goat anti-mouse IgG conjugated to horseradish peroxidase (Cappel), washed in TBS, and developed as described above. The blot reacting with the Apxl-specific monoclonal antibody was incubated with a 1:2000 dilution of goat anti-mouse IgG conjugated to alkaline phosphatase and developed as described previously (Frey et al., 1992).

LPS extraction and electrophoresis. LPS was isolated from A. pleuropneumoniae using a micro hot phenol-water extraction method, as previously described (Inzana, 1983). Purified LPS was electrophoresed through a 15% polyacrylamide separating gel containing urea, as described (Inzana et al., 1988). LPS electrophoretic profiles were visualized by staining the gel with ammoniacal silver (Tsai and Frasch, 1982).

Serum bactericidal assay. Sensitivity of A. pleuropneumoniae to the bactericidal activity of precolostral calf serum was determined. Percent viability of bacterial strains in 5, 10, 15, 20, 30, 40, and 50% precolostral calf serum was evaluated after 60 minutes incubation at 37° C.

Virulence study. Pigs 7 to 9 weeks of age were obtained from two local herds free from A. pleuropneumoniae infection and were distributed randomly into groups. Groups of pigs were housed in separate pens with no direct physical contact permitted between each group. The animal facilities at Virginia Polytechnic Institute and State University are operated and maintained in accordance with the requirements of the American Association for Accreditation of Laboratory Animal Care. For the challenge experiment, A. pleuropneumoniae strains were grown with shaking in Columbia broth (Difco Laboratories) supplemented with 5 μg/ml NAD attion at 7000×g and resuspended to approximately $10^9$ CFU/ml in PBS. Pigs were challenged intratracheally with 10 ml of a dilution of this suspension following mild sedation with Stresnil (Pittman-Moore, Inc., Washington Crossing, N.J.). Pigs were necropsied as soon as possible after death or immediately after euthanasia with sodium pentobarbital. Lung lesions were scored by a veterinary pathologist according to the following criteria: 0, unremarkable lungs (no gross lesions observed); 1+, 1–10% of lung tissue affected by some combination of congestion, edema, hemorrhage, consolidation, and/or pleuritis; 2+, 11–49% of lung tissue affected; 3+, 50–74% of lung tissue affected; 4+, 75% or greater of lung tissue affected. Lung samples were taken at necropsy from the right cranial-dorsal aspect of the caudal lobe and cultured on brain heart infusion medium containing NAD to detect the presence of A. pleuropneumoniae.

RESULTS

Identification and cloning of a serotype-specific A. pleuropneumoniae DNA region. To identify and clone A. pleuropneumoniae J45 DNA involved in capsular polysaccharide biosynthesis, Southern blot analyses were performed to identify an adjacent DNA region upstream (in the 5' direction) from the cpxDCBA gene cluster involved in the export of capsule polysacharide described above (FIGS. 10a–b and 11). It was expected this upstream DNA region would encode serotype-specific genes involved in capsular polysaccharide biosynthesis because the A. pleuropneumoniae capsulation (cap) locus seemed to be organized in a manner similar to the capsulation loci of Haemophilus influenzae type b and Neisseria meningitidis group B. BamHI-digested A. pleuropneumoniae J45 genomic DNA was probed with the digoxigenin-labeled 1.2 kb BamHI-XbaI fragment of pCW-1C that contained a portion of the cpxD gene. This cpxD-specific probe hybridized to a single, approximate 5.8 kb BamHI J45 genomic DNA fragment (data not shown). This 5.8 kb BamHI fragment was cloned into the BamHI site of pGEM-3Z from BamHI-digested J45 genomic DNA fragments in the range of 5.0–6.5 kb that were electroeluted (following electrophoretic separation) from an agarose gel. The resulting plasmid was designated pCW-11E and was restriction mapped (FIG. 1). A portion of the pCW-11 E insert DNA (the 1.2 kb BamHI-XbaI fragment) overlapped the DNA present on the insert of pCW-1C.

Figure 2:
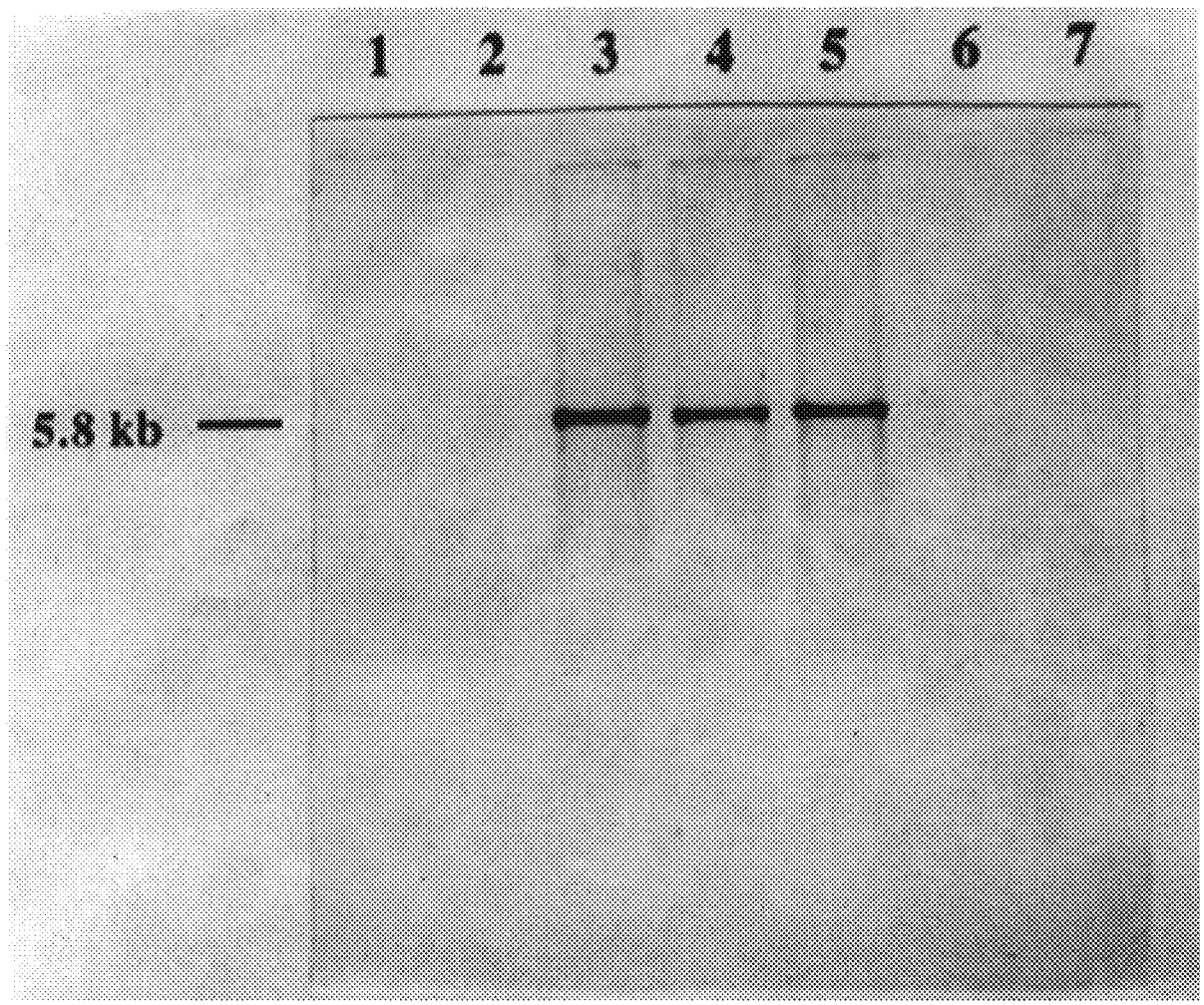
FIG. 2 is a southern blot analysis of *A. pleuropneumoniae* genomic DNA hybridized to the digoxigenin-labeled 2.1 kb BglII-StuI fragment of pCW11E. BamHI-digested genomic DNA from serotype 1 strain 4074 (lane 1), serotype 2 strain 1536 (lane 2), serotype 5a strain J45 (lane 3), serotype 5a strain K17 (lane 4), serotype 5 strain 178 (lane 5), serotype 7 strain 29628 (lane 6), and serotype 9 strain 13261 (lane 7) were hybridized with the probe as described below. The molecular mass of the hybridizing bands (in kb) is indicated.

BamHI-digested genomic DNA from several different A. pleuropneumoniae serotypes was hybridized with the 2.1 kb BglII-StuI fragment of pCW-11 E (FIG. 1) to determine the serotype-specificity of this DNA region (FIG. 2). The 2.1 kb BglII-StuI DNA fragment hybridized to a 5.8 kb BamHI genomic DNA fragment from three A. pleuropneumoniae serotype 5 strains tested, but not to genomic DNA from serotypes 1, 2, 7, and 9 (FIG. 2). Thus, the A. pleuropneumoniae DNA in pCW-11 E contained DNA that was specific to serotype 5 strains. Because this DNA was serotype-specific, it was likely to be involved in capsular polysaccharide biosynthesis.

Nucleotide sequence and analysis of a serotype-specific A. pleuropneumoniae DNA region. The nucleotide sequence of the 2.7 kb XbaI-EcoRV DNA fragment of pCW-11E was determined. This nucleotide sequence was combined with the nucleotide sequence of the 4.6 kb ClaI-XbaI fragment of pCW-1C and was examined for the presence of open reading frames (ORFs) not previously identified. The nucleotide sequence of the 3.2 kb HindIII-EcoRV fragment of pCW-11E containing newly identified ORFs is provided in FIG. 3. Two complete ORFs, designated cpsA and cpsB (cps for capsular polysaccharide synthesis), were identified upstream and on the opposite strand from the cpxD gene involved in A. pleuropneumoniae capsular polysaccharide export (FIG. 1 and FIG. 3). The AUG initiation codon of cpsB was 3 nucleotides downstream from the UAA termination codon of cpsA. An AUG initiation codon of a third potential ORF, cpsC, was identified 15 bases downstream from the UAA termination codon of cpsB. Shine-Dalgarno ribosome-binding consensus sequences (Shine and Dalgarno, 1974) were identified within 13 bases upstream of the AUG initiation codons of cpsA, cpsB, and cpsC (FIG. 3). A putative promoter, containing sequences similar to the E. coli $^{70}$-10 (TATAAT) and -35 (TTGACA) consensus sequences (Hawley and McClure, 1983) was identified upstream of cpsA (FIG. 3). The close proximity of cpsABC and the identification of a putative promoter upstream suggested that these ORFs may be co-transcribed. The G+C content for the DNA region encoding cpsABC was 28%.

The predicted polypeptides of cpsA and cpsB were comprised of 321 (CpsA) and 526 (CpsB) amino acids (FIG. 3). The predicted molecular masses of CpsA and CpsB were 36.9 and 61.7 kiloDaltons (kDa), respectively. Hydropathy plots demonstrated that CpsA and CpsB were relatively hydrophilic proteins, suggesting that these proteins may be associated with the A. pleuropneumoniae cytoplasmic compartment (data not shown). BLAST searches (Altschul et al., 1990) of the combined, nonredundant nucleotide and protein databases at the National Center for Biotechnology Information did not reveal any substantial homology between cpsABC at the nucleotide or amino acid level with other sequences in the databases (data not shown). However, a low level of homology (15% similarity) was observed between CpsA and the E. coli Rfb protein, an O-antigen glycosyltransferase involved in LPS biosynthesis (Cheah and Manning, 1993). A low level of homology (approximately 14% similarity) was detected between CpsB and the region 2 ORF 3 predicted protein product of the H. influenzae type b capsulation locus. The ORF 3 predicted protein is involved in the biosynthesis of the polyribosylribitol phosphate capsular polysaccharide of H. influenzae type b (Van Eldere et al., 1995). No significant homology was observed between the N-terminal 83 amino acids of CpsC and any proteins in the databases.

Figure 4:
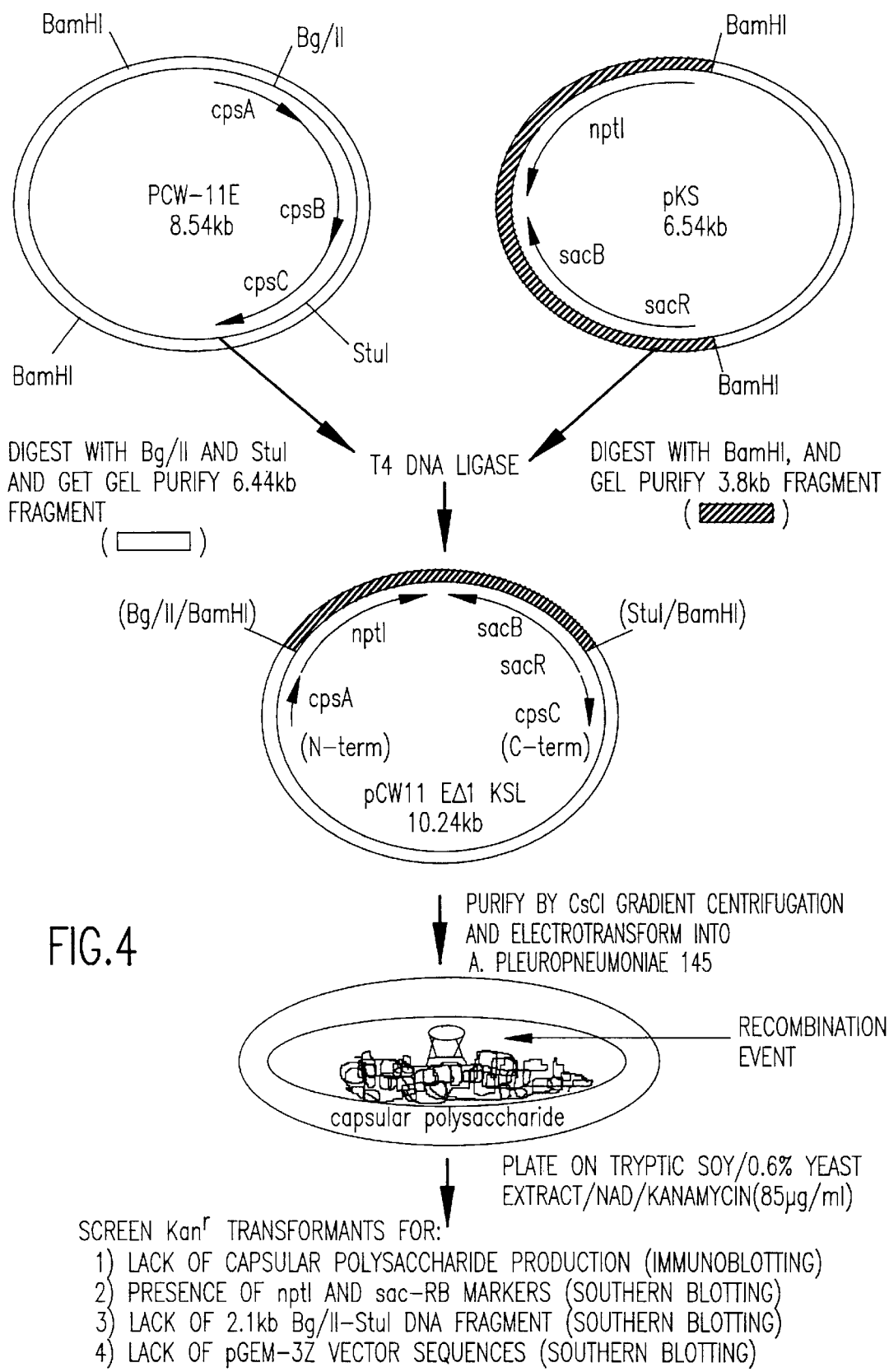
FIG. 4 describes construction of the suicide vector containing the deleted capsule synthesis DNA, pCW11 EΔ1 KS1, and production of noncapsulated mutants of A. pleuropneumoniae J45 by allelic exchange. The pCW11EΔ1KS1 plasmid vector was constructed by digesting pCW-11E with BglII and StuI, making the ends blunt-ended, and ligating the large 6.4 kb fragment to the 3.8 kb BamHI fragment of pKS (also made bluntended) containing the nptl-sacRB (Kan$^r$ Suc$^s$) cartridge. Restriction sites in parentheses indicate the original ends of the fragments ligated in pCW11EΔ1KS1. The pCW11EΔ1KS1 vector was electrotransformed into A. pleuropneumoniae, and noncapsulated Kan$^r$ transformants were screened by lack of iridescence on media containing 85 µg/ml of kanamycin.

Production of kanamycin-resistant, noncapsulated A. pleuropneumoniae serotype 5a transformants. FIG. 4 schematically outlines the procedures used to produce recombinant, noncapsulated *A. pleuropneumoniae* J45 mutants by homologous recombination and allelic exchange. The vector pCW11EΔ1 KS1 was first constructed to use as a nonreplicating, suicide vector to promote the exchange of wild type *A. pleuropneumoniae* capsulation DNA with genetically-altered *A. pleuropneumoniae* capsulation DNA by a double homologous recombination crossover event. The pCW11 EΔ1 KS1 vector was constructed by first digesting pCW-11 E with BglII and Stul to create a large deletion in serotype-specific *A. pleuropneumoniae* capsulation DNA. The ends of this digested DNA were made blunt ended, and the large 6.4 kb fragment was ligated to the 3.8 kb BamHI fragment of pKS (also made blunt ended) containing the nptl-sacR-sacB cartridge. This cartridge contains the Tn903 nptl gene before which is known to confer kanamycin resistance (Kan$^r$) to *A. pleuropneumoniae* (Tascon et al., 1994), and the sacRB sequences that confer sucrose sensitivity (Suc$^s$) to many gram-negative bacteria (Gay et al., 1983; Ried and Collmer, 1987). The deletion created in pCW11EΔ1KS1 spanned cpsABC (FIG. 1, FIG. 4) and was, therefore, likely to affect the protein products of these ORFs.

The pCW11EΔ1KS1 vector did not replicate in *A. pleuropneumoniae* and, therefore functioned as a suicide vector. After PCW11 EΔ1 KS1 was electroporated into *A. pleuropneumoniae* J45, seven kanamycin-resistant transformants were obtained after the recovery mixtures were incubated at 37° C. for 2 days. Four of these kanamycin resistant J45 transformants were noniridescent when visualized on plates with an obliquely transmitted light source, suggesting that these transformants were noncapsulated (data not shown). The medium used to grow *A. pleuropneumoniae* prior to electroporation with pCW11EΔ1KS1 was a factor since noncapsulated kanamycin-resistant transformants were never obtained when *A. pleuropneumoniae* was grown in brain heart infusion supplemented with NAD.

Genotypic characterization of the kanamycin-resistant *A. pleuropneumoniae* transformants. Preliminary colony hybridization analyses of the seven kanamycin-resistant transformants revealed that the four transformants which appeared noncapsulated (by visual inspection) hybridized with an nptl-specific DNA probe (the 1.24 kb Pstl fragment of pKS), but not with probes specific for pGEM-3Z (the 1.1 kb BglII fragment pGEM-3Z) or the serotype-specific 2.1 kb BglII-StuI fragment of pCW-11E (data not shown). These results indicated that a double recombination event had occurred in each of these four kanamycin-resistant transformants. In contrast, colonies of the other three kanamycin-resistant transformants hybridized to probes specific for the nptI gene, pGEM-3Z, and the 2.1 kb BglII-StuI fragment of pCW-11E, suggesting that a single cross over had occured and the entire pCW11EΔ1KS1 suicide vector had integrated into the chromosome of these transformants (data not shown). Southern blot analyses of genomic DNA purified from the four kanamycin-resistant, potentially noncapsulated transformants (using the probes described above) were identical, indicating that the same double recombination event had occurred in each of these transformants. One of these transformants was randomly selected for further study and was designated J45-100.

Figure 5:
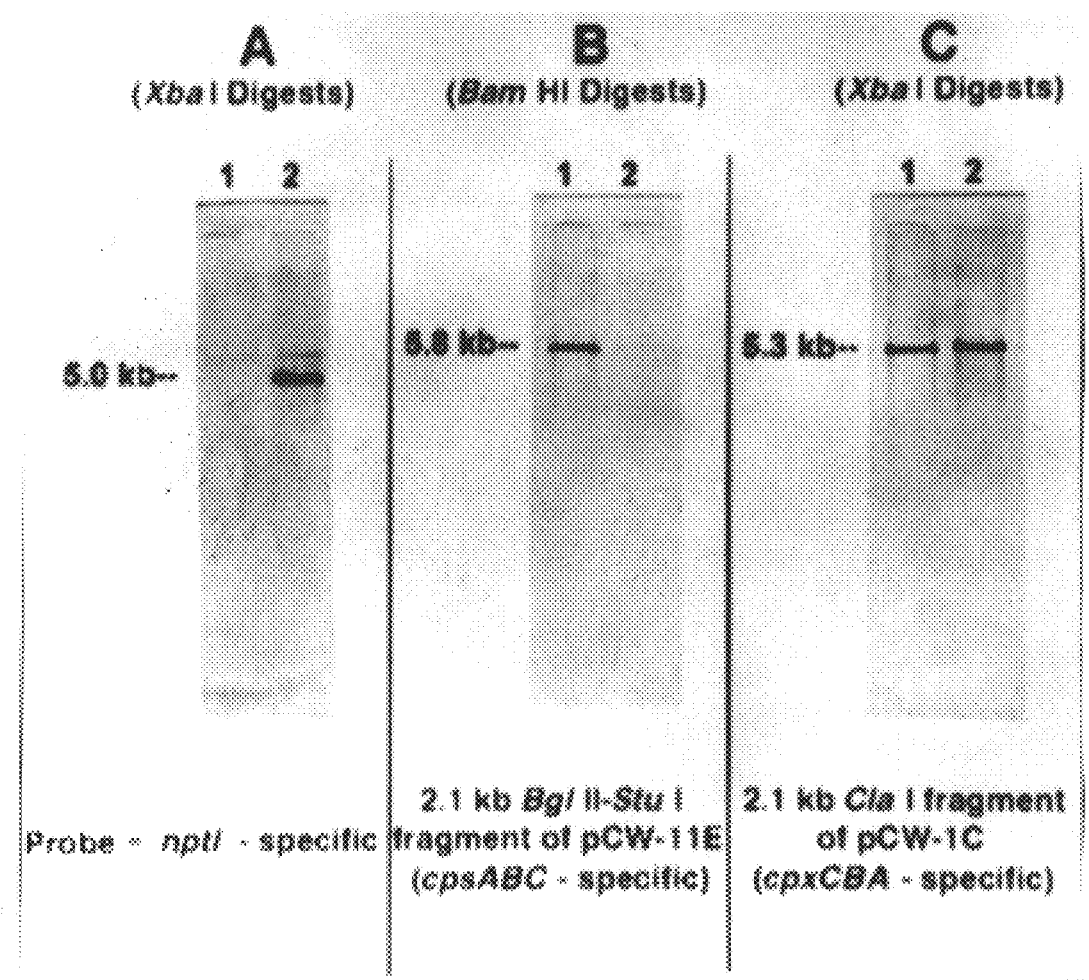
FIG. 5 is a southern blot analysis of genomic DNA isolated from A. pleuropneumoniae J45 (lane 1) or J45-100 (lane 2) with digoxigenin-labeled probes specific for nptl or portions of the A. pleuropneumoniae capsulation locus. A. pleuropneumoniae J45 (lane 1) or J45-100 (lane 2) genomic DNA was digested with XbaI (panels A and C) or BamHI (panel B), and hybridized with either the 1.24 kb PstI fragment of pKS (nptl-specific), panel A; the 2.1 kb BglII-StuI fragment of pCW-11E (cpsABC-specific, see FIG. 1), panel B; or the 2.1 kb C/al fragment of pCW-1C (cpxCBA-specific, see FIG. 3.2), panel C.

Southern blot analyses of genomic DNA isolated from J45 and J45-100 with DNA probes specific for the nptI gene, the 2.1 kb BglII-StuI fragment of pCW-11E, and the 2.1 kb ClaI fragment of pCW-1C were performed (FIG. 5). The nptI-specific DNA probe hybridized to a 5.0 kb fragment of XbaI digested J45-100 DNA, but not to J45 DNA, verifying that the nptI marker was in the chromosome of J45-100 (FIG. 5A). The hybridization of the nptI probe to a 5.0 kb XbaI J45-100 genomic DNA fragment was consistent with the size of this XbaI fragment in the pCW11E~1KS1 suicide vector used to produce J45-100. The 2.1 kb BglII-StuI fragment of pCW-11E hybridized to a 5.8 kb fragment of BamHI-digested J45 but not to J45-100 DNA, verifying that this fragment was deleted in J45-100 (FIG. 5B). The probe specific for the cpxCBA genes (the 2.1 kb ClaI fragment of pCW-1C) involved in capsular polysaccharide export hybridized to a 5.3 kb XbaI fragment of both J45 and J45-100 (FIG. 5C). This result verified that this portion of the *A. pleuropneumoniae* capsulation locus was unaffected by the double recombination event that had occurred within the adjacent DNA region. A probe specific for pGEM-3Z did not hybridize to genomic DNA from either J45 or J45-100, verifying that no vector DNA was contained in the genome of J45-100. Collectively, these DNA hybridization results indicated that the desired double recombination event and allelic exchange had occurred in J45-100.

Figure 6:
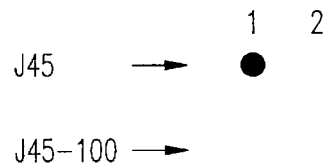
FIG. 6 is a colony immunoblot of A. pleuropneumoniae J45 and J45-100 reacted with a capsular polysaccharide specific swine antiserum. Approximately $5\times10^5$ (lane 1) or $5\times10^4$ (lane 2) CFU per well were applied to a nitrocellulose membrane. The membrane was lysed in chloroform and incubated with a swine antiserum that contained antibodies to the serotype 5a capsular polysaccharide but not other A. pleuropneumoniae surface antigens.

Phenotypic characterization of the *A. pleuropneumoniae* kanamycin-resistant transformant, J45-100. J45-100 was evaluated for capsular polysaccharide production by colony immunoblotting and latex agglutination. Antiserum containing antibodies specific for the *A. pleuropneumoniae* serotype 5a capsular polysaccharide, but not other bacterial surface components, reacted with J45 but did not react with J45-100 (FIG. 6). Because the bacterial colonies on the membrane had been lysed in chloroform, these results indicated that J45-100 did not produce intracellular or extracellular capsular polysaccharide. Whole or sonicated J45-100 did not agglutinate latex beads that were covalently conjugated to purified antibody to the serotype 5a capsular polysaccharide of *A. pleuropneumoniae* (Inzana, 1995), whereas J45 whole cells and sonicated J45-C cells strongly agglutinated the latex bead reagent (data not shown). These results verified that the deletion engineered into the cap locus of *A. pleuropneumoniae* J45-100 resulted in the loss of capsular polysaccharide biosynthesis. Furthermore, these results indicated that a noncapsulated mutant of J45 isolated after ethyl methanesulfonate mutagenesis (Inzana et al., 1993a), J45-C, produced intracellular but not extracellular capsular polysaccharide.

Figure 7:
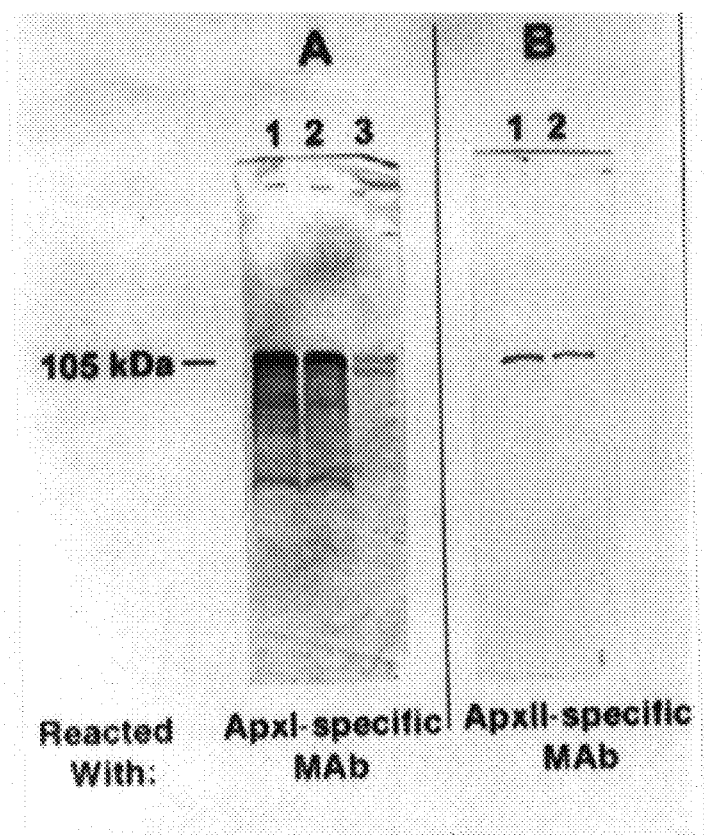
FIG. 7 shows immunoblots of A. pleuropneumoniae J45 (lane 1) and J45-100 (lane 2) concentrated culture supernatants containing predominately the exotoxins Apxl and Apxll. Panel A was reacted with an Apxl-specific monoclonal antibody, and panel B was reacted with an Apxll-specific monoclonal antibody. In panel A, the concentrated culture supernatant of A. pleuropneumoniae serotype 2 strain 1536 (lane 3) was included as a negative control because this serotype does not synthesize Apxl. The blot in panel A was reacted with the Apxl-specific monoclonal antibody.
Figure 8:
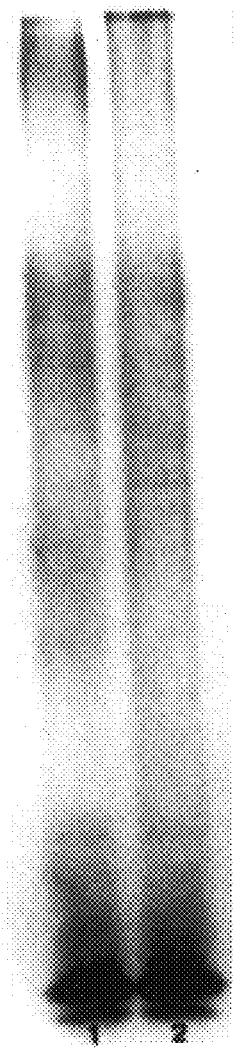
FIG. 8 shows the electrophoretic profiles of LPS isolated from A. pleuropneumoniae J45 (lane 1) and the recombinant noncapsulated mutant J45-100 (lane 2). LPS was electrophoresed through a 15% separating gel and stained with ammoniacal silver.

Apx toxin expression and the LPS electrophoretic profiles of J45 and J45-100 were compared to determine if the mutation engineered into the cap locus of J45-100 affected these important virulence determinants. No difference in secretion of the 105 kDa ApxI and ApxII toxin proteins into culture supernatant was detected between J45 and J45-100 (FIG. 7). In addition, no difference in the LPS electrophoretic profiles of J45 and J45-100 was detected (FIG. 8).

Figure 9:
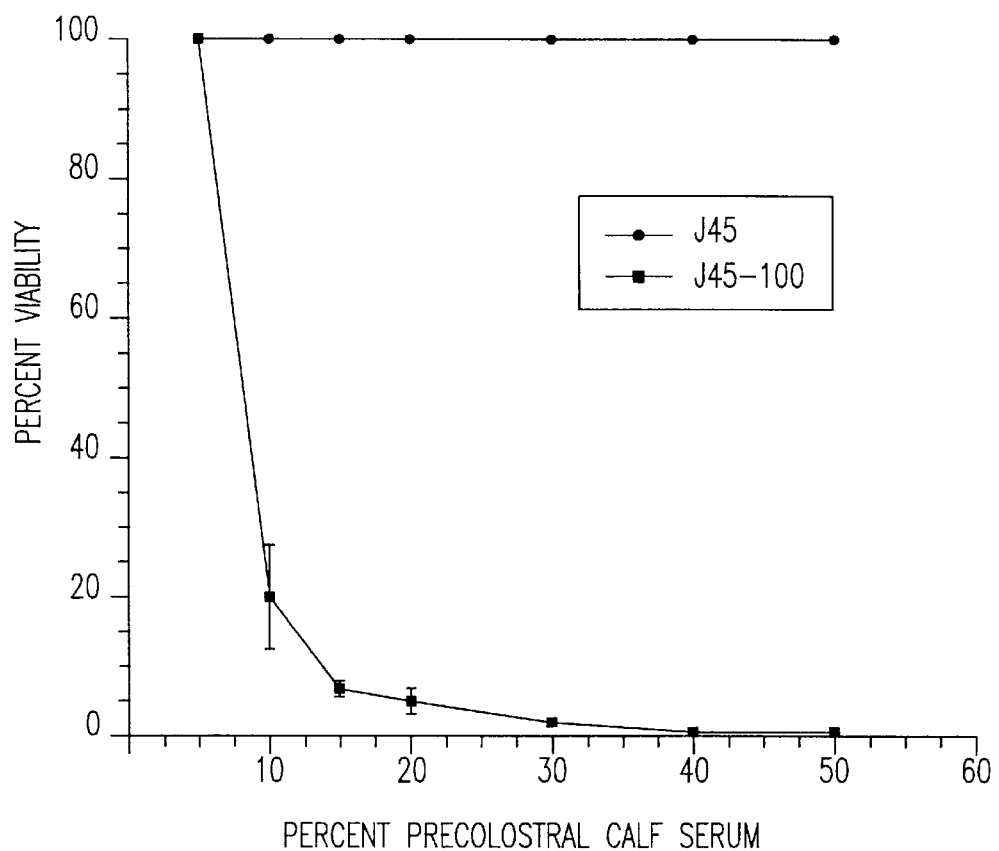
FIG. 9 shows the bactericidal activity of precolostral calf serum for A. pleuropneumoniae J45 and J45-100. Percent viability of bacterial strains was evaluated after 60 minutes incubation at 37° C. Each data point represents the mean of three separate experiments performed in duplicate. Error bars represent the standard deviation for each mean. The maximum percent viability recorded for J45 was 100%, although these values were typically higher because the bacteria usually grew during the experiment. Values greater than 100% were not recorded because they could not be accurately determined.

The growth of J45 and J45-100 in TSY-N and the sensitivity of J45 and J45-100 to the bactericidal activity of precolostral calf serum were examined to determine the effect of loss of encapsulation on these phenotypic properties. Growth curves of J45 and J45-100 in TSY-N were similar but not identical (data not shown). However, viable plate counts demonstrated that during the logarithmic phase of growth, J45-100 grew faster (generation time=ca. 23 minutes) than the parent encapsulated strain, J45 (generation time=ca. 28 minutes) (data not shown). The recombinant noncapsulated mutant, J45-100, was efficiently killed within 60 minutes in 10 to 50% precolostral calf serum as a complement source, whereas the encapsulated parent strain, J45, was not killed (FIG. 9).

The sucrose sensitivity of J45-100 was examined to determine whether the sacRB sequences could function as a counterselectable marker in *A. pleuropneumoniae* and subsequently induce the excision of the nptI-sacRB cartridge from the J45-100 chromosome. Broth-grown J45-100 grew very heavily when plated directly or when diluted and then plated on TSY-N or Luria-Bertani (to which 5 llg/ml NAD was added) medium containing 5% or 8% sucrose. The presence of the sacRB sequences in the chromosome of J45-100 was verified by Southern blotting. These results suggested that either the sacRB marker was not expressed in *A. pleuropneumoniae* or possibly that the levan product formed by the sacRB levansucrase in the presence of sucrose was not toxic to J45-100.

Intratracheal challenge of pigs with the recombinant *A. pleuropneumoniae* noncapsulated mutant, J45-100. The recombinant noncapsulated mutant, J45-100, did not cause any mortality in pigs when administered at doses 3 and 6 times (1.45×107 CFU and 2.95×107 CFU, respectively) the 50% lethal dose (LD50) of the encapsulated parent strain, J45 (5×106 CFU) (Inzana et al., 1993a) (Table 2). In contrast, all three of the pigs challenged with 6.5 times the $LD_{50}$ of J45 developed severe lung lesions and died (Table 2).

TABLE 2

Virulence of *A. pleuropneumoniae* J45 and J45-100 for pigs

| Challenge Strain | Challenge Dose | Mean Lung Lesion Score | Number positive/total number tested | |
|---|---|---|---|---|
| | | | Mortality | Recovery[a] |
| J45 | 1.6–3.30 × 10⁷ CFU[b] | 4+ | 3/4[c] | 4/4 |
| J45-100 | 1.5 × 10⁷ CFU | 0 | 0/5 | 0/5 |
| J45-100 | 3.0 × 10⁷ CFU | 1+ | 0/5 | 2/5[d] |
| J45-100 | 8.4 × 10⁷ CFU | 1+ | 1/4[e] | 4/4[b] |
| J45-100 | 1.8 × 10⁸ CFU | 2+ | 0/4 | 4/4[d] |
| J45-C | 1.7 × 10⁸ CFU | 1+ | 0/2 | 2/2[d] |

[a]Recovery of the challenge strain from lung samples taken at necropsy. Pigs challenged with J45-100 were necropsied 4 days post-challenge.
[b]This dose is 6.6 times the 50% lethal dose (5 × 10⁶ CFU) reported in a previous study (Inzana et al., 993a).
[c]All of the pigs in this group died within 36 hours post-challenge.
[d]*A. pleuropneumoniae* was recovered from the lungs, and was confirmed to be noncapsulated by lack of iridescence and failure to agglutinate serotype 5-specific sensitized latex particles.
[e]Necropsy of the one pig that died indicated that death was due to misadministration of challenge dose.

The five pigs challenged with the lower dose of J45-100 (1.45×107 CFU) did not exhibit any clinical symptoms characteristic of swine pleuropneumonia and did not develop any lung lesions. Furthermore, *A. pleuropneumoniae* was not cultured from lung samples taken four days post-challenge at necropsy. Two of the five pigs challenged with the higher dose of J45-100 (2.95×10⁷ CFU) were clinically normal and no lung lesions were observed at necropsy. One pig in this group challenged with the higher J45-100 dose exhibited moderate dyspnea, and at necropsy some lung congestion and slight hemorrhage were observed (lung lesion score=1+). The remaining two pigs in this group exhibited mild dyspnea, and at necropsy some pleuritis and consolidation were observed (lung lesion score=2+). *A. pleuropneumoniae* J45-100 was cultured only from these two pigs with the most severe lung lesions. The bacteria recovered from these pigs did not agglutinate the serotype 5a latex bead agglutination reagent. Thus, the recovered bacteria were still noncapsulated, indicating that J45-100 did not revert to the encapsulated phenotype in vivo.

While nptI (confers resistance to kanamycin) and SacB/SacR (confers sensitivity to sucrose) genes were cloned into the deletion site, these genes were only intended to be used as marker genes. Alternative marker genes may also be employed. It may be preferable to avoid using an antibiotic resistant marker such as nptI for health and safety related reasons, or to provide a mechanism for curing or inactivating the antibiotic marker. Suitable non-antibiotic markers might include mercury resistance.

The non-capsulated strain of *Actinobacillus pleuropneumoniae* serotype 5 produced according to the above procedures only produces two of the three toxins made by *Actinobacillus pleuropneumoniae*. While the modified *Actinobacillus pleuropneumoniae* is protective and immunogenic, it may also be useful to clone the third RTX toxin gene into the deletion site. This may be done by cloning the RTX toxin gene into the kanamycin gene cassette of strain J45-100, thus inactivating the kanamycin gene.

The vaccine should preferably be provided in a form similar to other vaccines well known in the art. It is preferable that the vaccine will be bottled as a lyophilized mixture, and can include one or more serotypes of mutant strains. To preserve viability, a substance such as Columbia broth, trehalose, or albumin, glycerol, or some other agent would be included. The contents of the lyophilized mixture would only need to be rehydrated with sterile water or saline and injected (intramuscular, intravenous, intraperitoneal, subcutaneous, etc.). The vaccine may also be formulated for other modes of administration as well (e.g., oral, transdermal, sublingual, etc.) using appropriate carrier matrixes (e.g., starch, polsaccharides, oils, liposomes, gums, etc.).

The dose of the vaccine provided to an animal will depend on such factors as the age or sex of the animal, and the mode of delivery. In all cases, a sufficient quantity of the live, avirulent, non-capsulated *Actinobacillus pleuropneumoniae* should be provided to give rise to an immunogenic response in the vaccinated animal. Successful results have been obtained with 2 immunizations 2 to 3 weeks apart of $10^9$ colony forming units.

While the invention has been described in terms of its preferred embodiments, those skilled in the art will recognize that the invention can be practiced with modification within the spirit and scope of the appended claims.

We claim:

1. A vaccine comprised of an avirulent, non-capsulated serotype 5 *Actinobacillus pleuropneumoniae* bacteium, said bacterium lacking DNA sequences coding for capsule synthesis.

2. A method of immunizing swine against pleuropneumonia, comprising the step of administering to said swine an immunogenic dose of a vaccine comprising an avirulent, non-capsulated serotype 5 *Actinobacillus pleuropneumoniae* bacterium which lacks DNA sequences coding for capsule synthesis.

3. The method of claim 2 wherein said step of administering is achieved by injecting the vaccine intramuscularly or subcutaneously.

4. A method of preparing a vaccine to prevent diseases caused by *Actinobacillus pleuropneumoniae* serotype 5 bacteria, comprising the steps of:

identifying genes encoding for capsule synthesis in said bacteria; and deleting said genes in said bacteria encoding for capsule synthesis to produce non-capsulated mutants of said bacteria.

* * * * *

UNITED STATES PATENT AND TRADEMARK OFFICE
CERTIFICATE OF CORRECTION

PATENT NO. : 6,086,894

DATED : July 11, 2000

INVENTOR(S) : Inzana, et al

It is certified that error appears in the above-identified patent and that said Letters Patent is hereby corrected as shown below:

Claim 1, line 3, "bacteium" should read ---- bacterium ----.

Signed and Sealed this

Twenty-ninth Day of May, 2001

*Attest:*

NICHOLAS P. GODICI

*Attesting Officer*    *Acting Director of the United States Patent and Trademark Office*